(12) United States Patent
Awrey et al.

(10) Patent No.: US 6,797,523 B2
(45) Date of Patent: Sep. 28, 2004

(54) METHODS FOR SYSTEMATIC IDENTIFICATION OF PROTEIN—PROTEIN INTERACTIONS

(75) Inventors: Donald E. Awrey, Mississauga (CA); Jack Greenblatt, Toronto (CA)

(73) Assignee: Affinium Pharmaceuticals, Inc., Toronto (CA)

(*) Notice: Subject to any disclaimer, the term of this patent is extended or adjusted under 35 U.S.C. 154(b) by 148 days.

(21) Appl. No.: 09/727,812

(22) Filed: Nov. 30, 2000

(65) Prior Publication Data

US 2002/0102741 A1 Aug. 1, 2002

(51) Int. Cl.[7] .............................................. G01N 33/543
(52) U.S. Cl. ...................... 436/518; 436/514; 436/161; 210/198.2; 210/656; 435/7.1
(58) Field of Search ........................... 435/7.1; 436/514, 436/518, 524, 173, 174, 161, 63; 210/198.2, 635, 656; 204/601

(56) References Cited

U.S. PATENT DOCUMENTS

| | | | | |
|---|---|---|---|---|
| 5,705,813 | A | 1/1998 | Apffel et al. | ................ 250/288 |
| 6,281,493 | B1 | * 8/2001 | Vestal et al. | ................ 250/287 |

FOREIGN PATENT DOCUMENTS

| | | |
|---|---|---|
| WO | WO 97/01755 | 1/1997 |
| WO | WO 00/11208 | 3/2000 |

OTHER PUBLICATIONS

Patterson et al, Application of combined mass spectrometry and partial amino acid sequence to the identification of gel–separated proteins, Electrophoresis, 1996, 17, 877–891.*
Koch et al.; "A Role for Ctr9p and Paf1p in the Regulation of G1 Cyclin Expression in Yeast", Nucleic Acids Research 27(10): 2126–2134, (1999).
Probert and Johnson; "Identification of a 47 kDa Fibronectin–Binding Protein Expressed by Borrelia Burgdorferi Isolate B31", Molecular Microbiology 30(5):1003–1015, (1998).
International Search Report Completed on Mar. 20, 2003 and Mailed on Apr. 9, 2003.
Archambault et al.; "An Essential Component of a C–Terminal Domain Phosphatase that Interacts with Transcription Factor IIF in Saccharomyces Cerevisiae", Proc. Natl. Acad. Sci. USA, 94: 14300–14305, (Dec. 1997).

Biemann Klaus; "Contributions of Mass Spectrometry to Peptide and Protein Structure", Biomedical and Environmental Mass Spectrometry 16: 99–111, (1998).
Delcher et al.; "Improved Microbial Gene Identification with Glimmer", Nucleic Acids Research 27(23): 4636–4641, (1999).
Edwards et al.; "Protein Production: Feeding the Crystallographers and NMR Spectroscopists", Nature Structural Biology, 7: 970–972, (2000).
Falick et al.; "Low–Mass Ions Produced From Peptides by High—Energy Collision–Induced Dissociation in Tandem Mass Spectrometry", J. Am. Soc. Mass. Spectrom. 4: 882–893, (1993).
Formosa et al.; "Using Protein Affinity Chromatography to Probe Structure of Protein Machines", Methods in Enzymology 208: 24–45, (1991).
Griffin et al.; "Direct Database Searching with MAL-DI–PSD Spectra of Peptides", Rapid Communications in Mass. Spectrometry 9: 1546–1551 (1995).
Mosbach et al.; "Formation of Proinsulin by Immobilized *Bacillus Subtilis*", Nature, 302: 543–545, (Apr. 7, 1993).
Palva et al.; "Secretion of Interferon by *Bacillus Subtilis*", Gene 22 : 229–235, (1983).
Patterson D. Scott; "Matrix–assisted Laser–desorption/ ionization Mass Spectrometric Approaches for the Identification of Gel–Separated Proteins in the 5–50 pmol range", Electrophoresis 16: 1104–1114, (1995).
Shevchenko et al.; "Mass Spectrometric Sequencing of Proteins From Silver–Stained Ployacrylamide Gels", Anal. Chem. 68: 850–858, (1996).
Sopta et al.; "Isolation of Three Proteins That Bind to Mammalian RNA Polymerase II", The Journal of Biological Chemistry, 260(18): 10353–10360, (Aug. 25, 1995).
Yates et al.; "Peptide Mass Maps: A Highly Informative Approach to Protein Identification", Analytical Biochemistry 214: 397–408, (1993).

* cited by examiner

*Primary Examiner*—Long V. Le
*Assistant Examiner*—Gary W. Counts
(74) *Attorney, Agent, or Firm*—Foley Hoag LLP

(57) ABSTRACT

The present invention relates to a method for identifying protein—protein interactions. The interacting proteins are isolated by affinity chromatography and identified by mass spectrometry. The affinity chromatography method allows for the purification of unknown interacting proteins which are identified using mass spectrometric techniques. The invention provides a method for the high throughput analysis of protein—protein interactions that lends itself to automation.

19 Claims, 21 Drawing Sheets

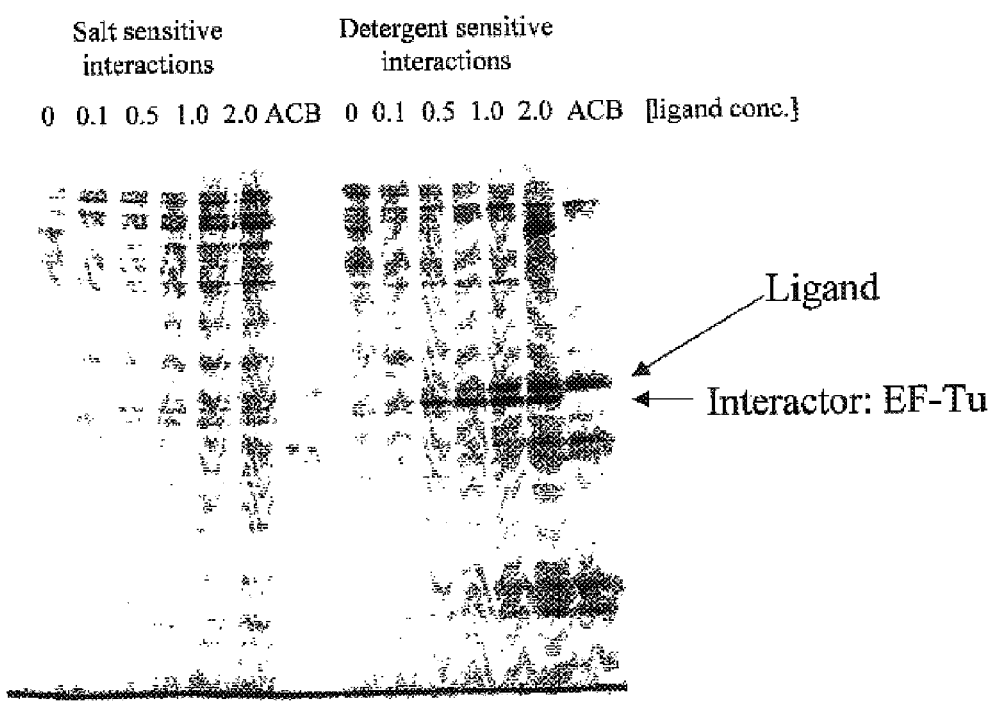
Figure 1. Interactions with SA0005

Figure 2: Interactions with SA0005
MALDI-TOF Mass Spectrum of Interactor (EF-Tu)
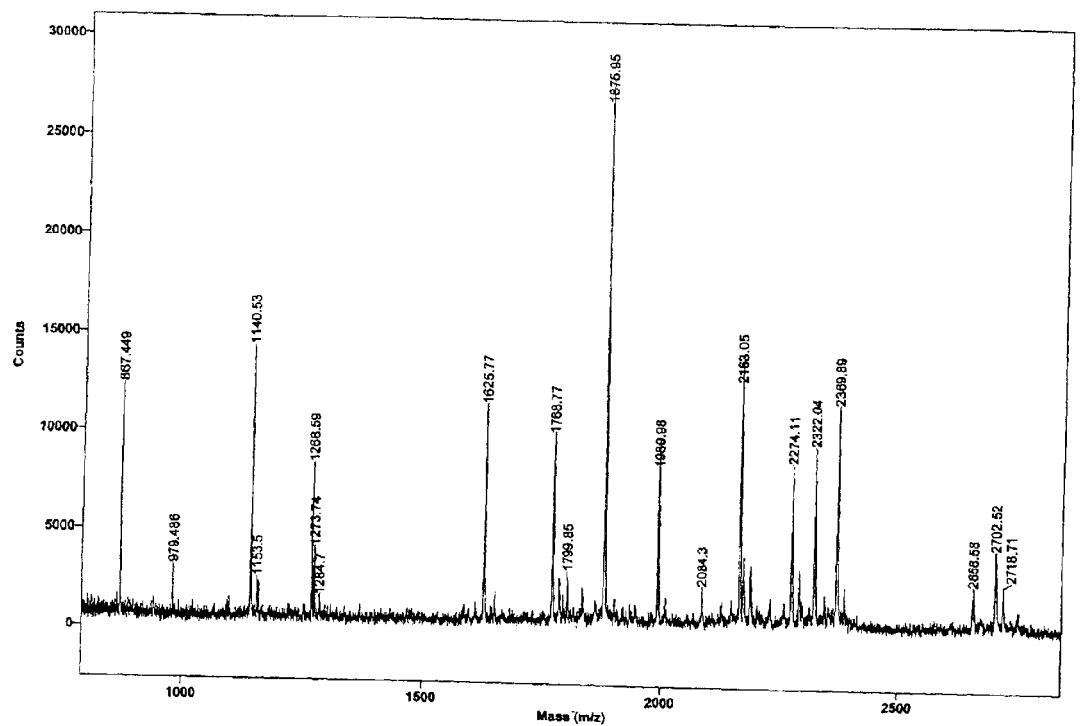

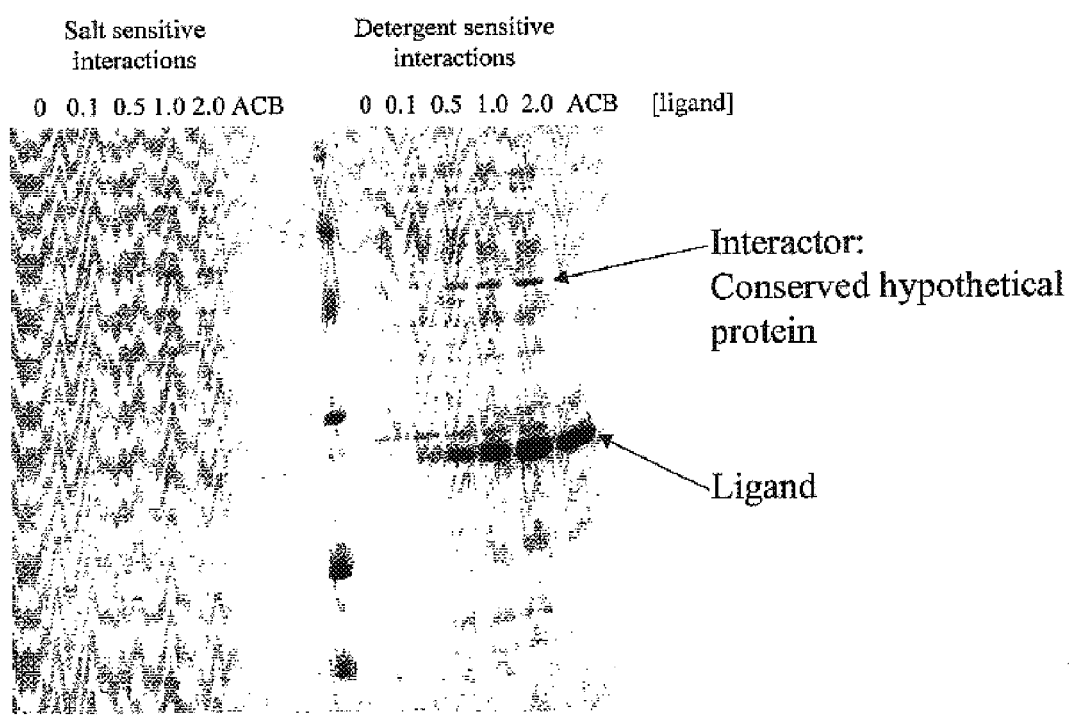
Figure 3. Interactions with SA0146

Figure 4: Interactions with SA0146
MALDI-TOF Mass Spectrum of Interactor
(conserved hypothetical protein)
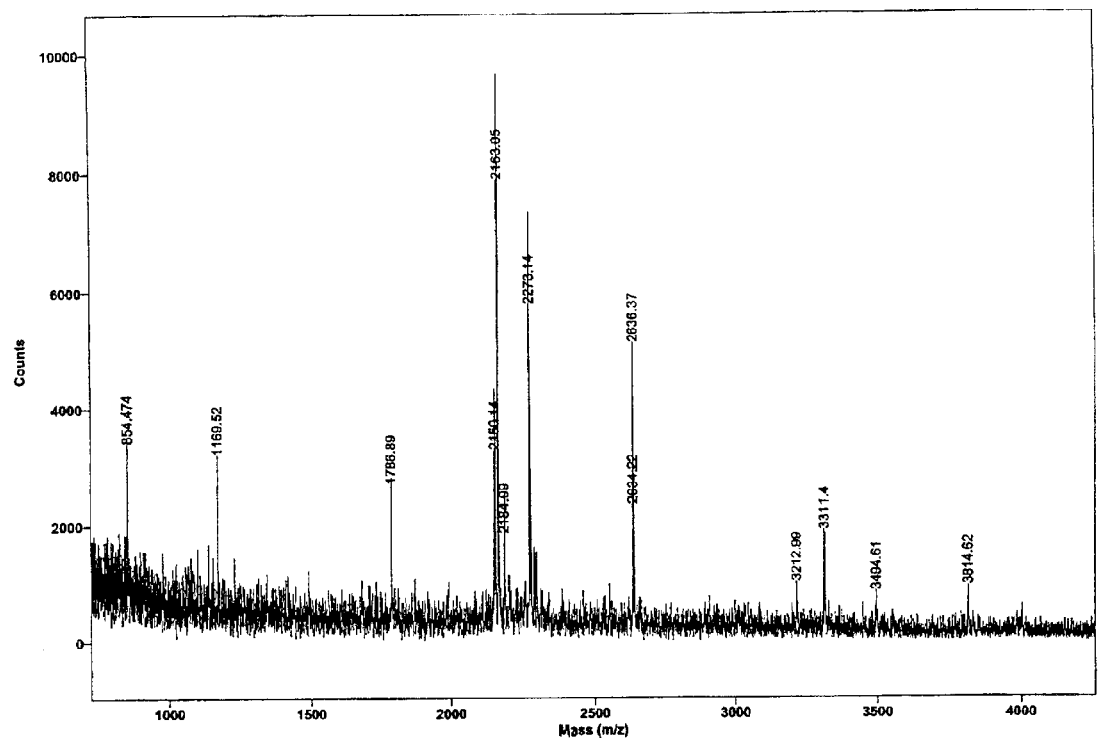

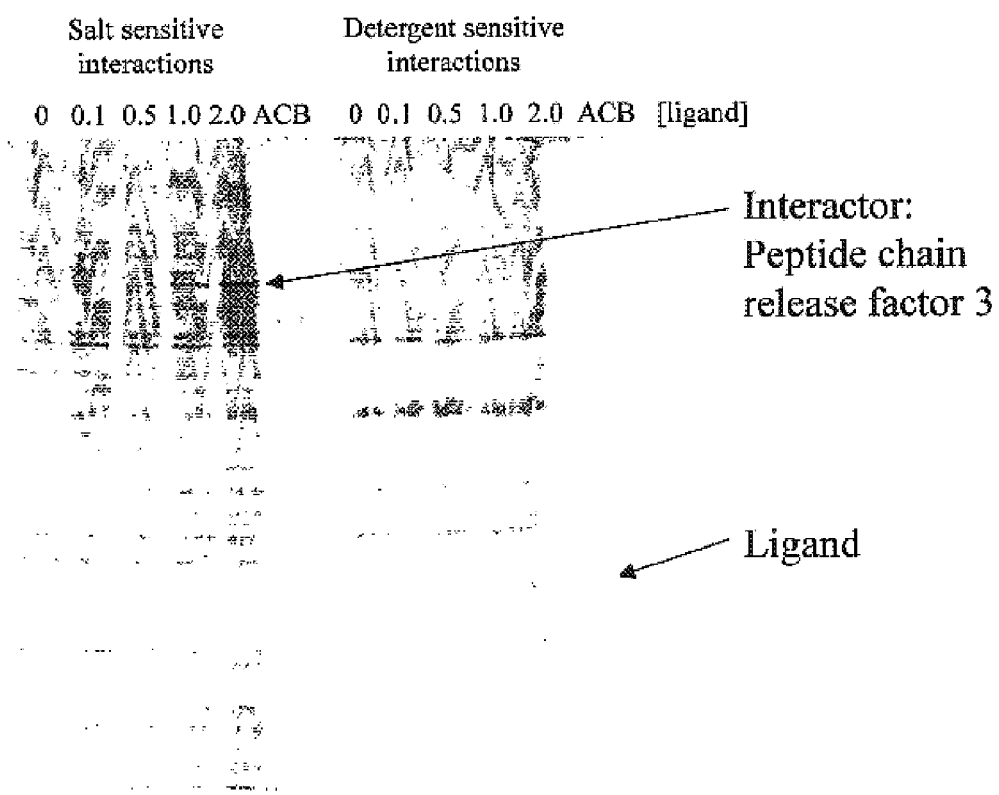

Figure 6: Interactions with SA0203
MALDI-TOF Mass Spectrum of Interactor
(peptide chain release factor 3)
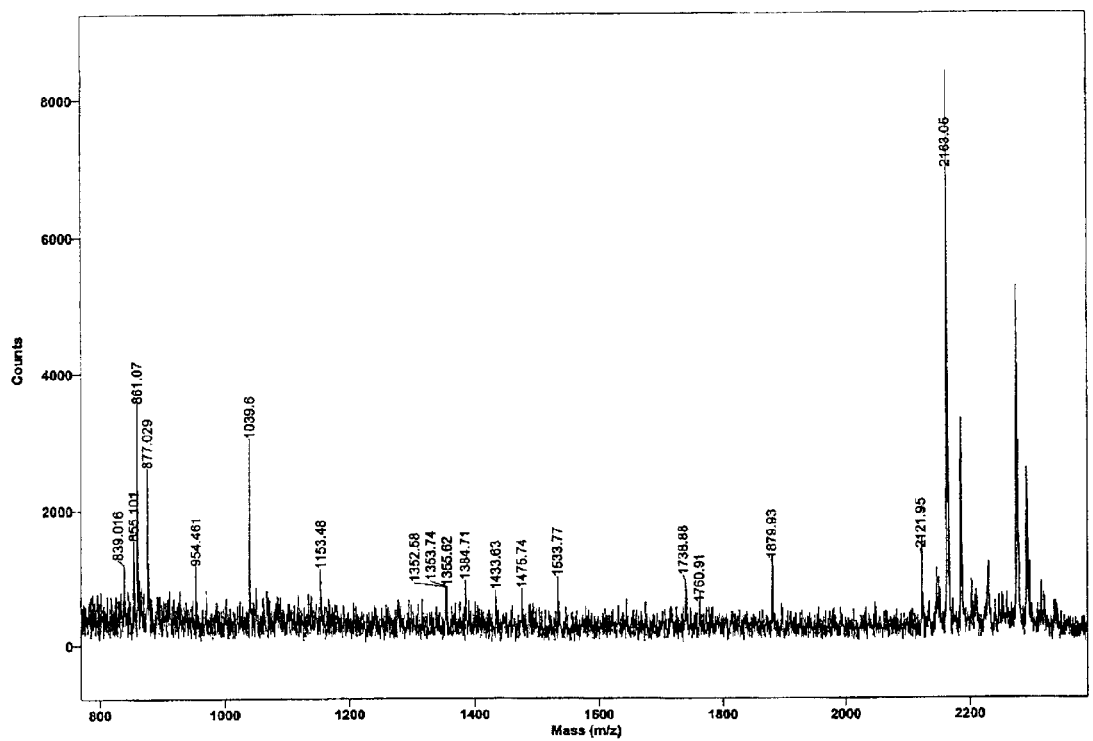

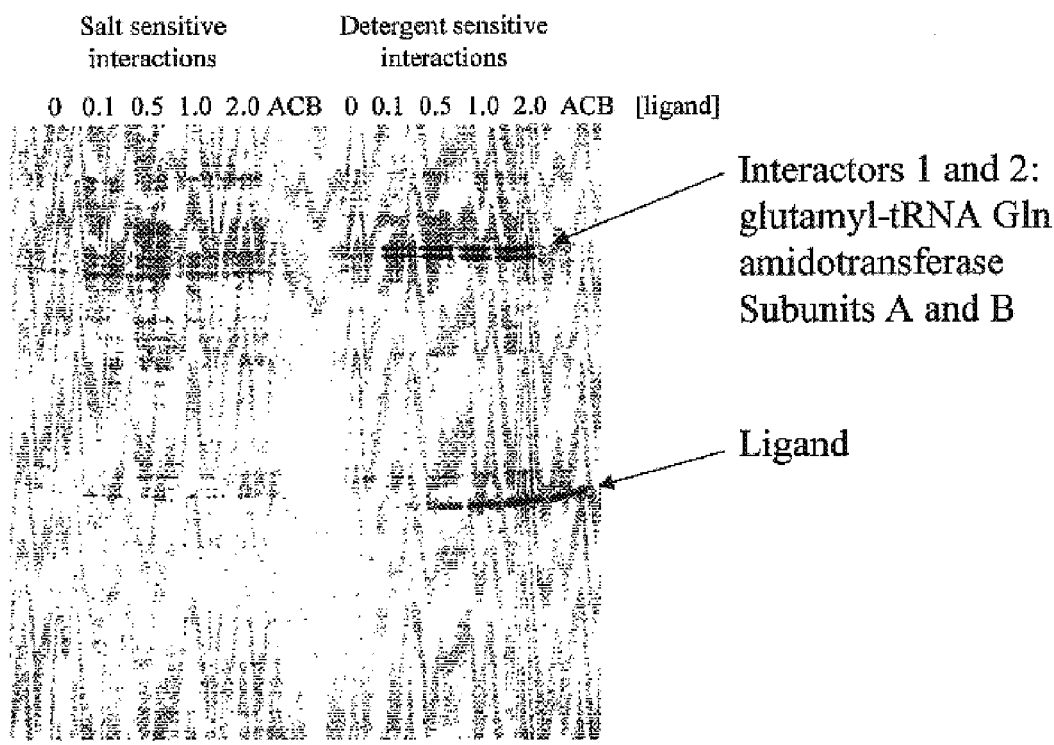
Figure 7: Interactions with SA0276

Figure 8: Interactions with SA0276
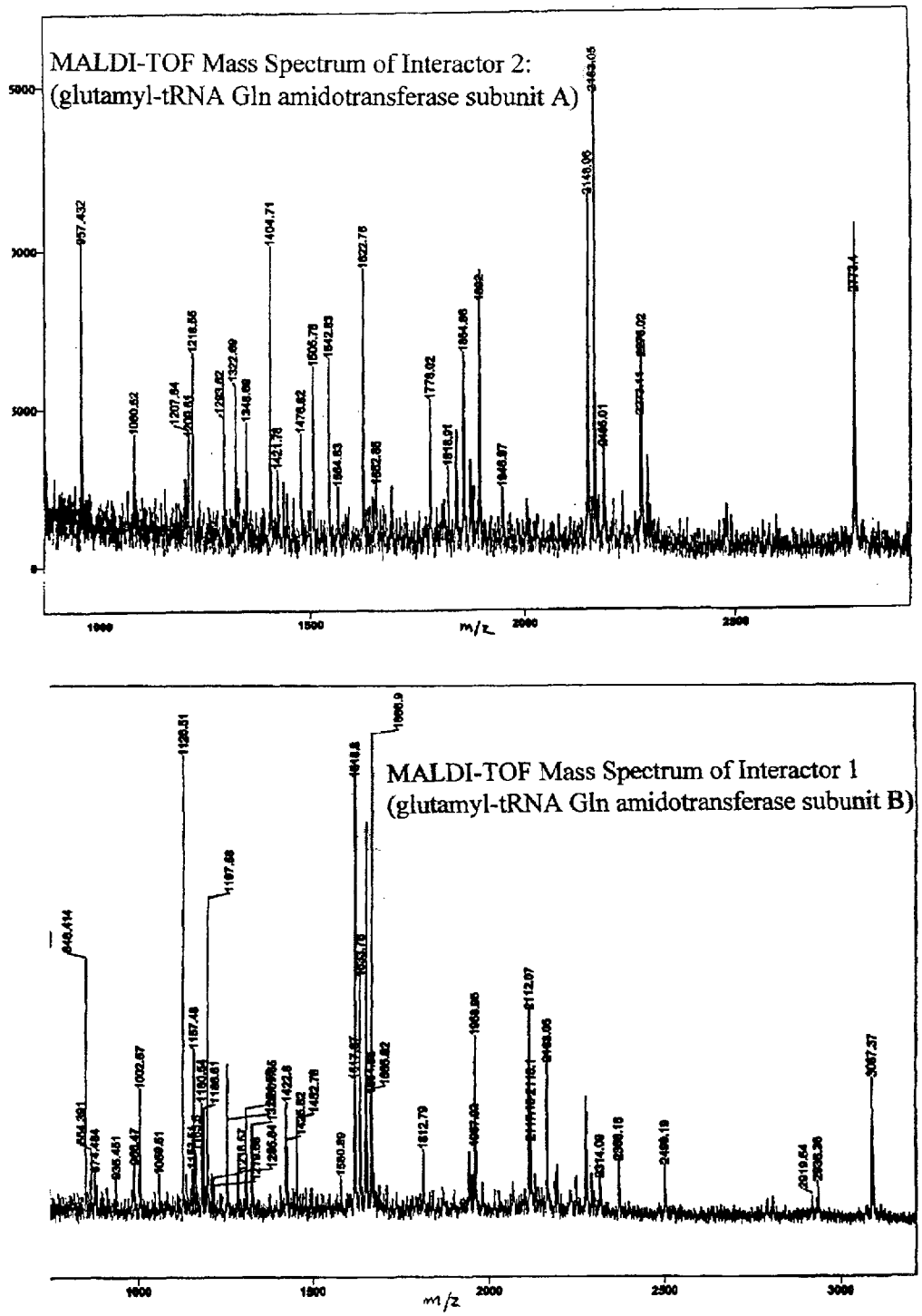

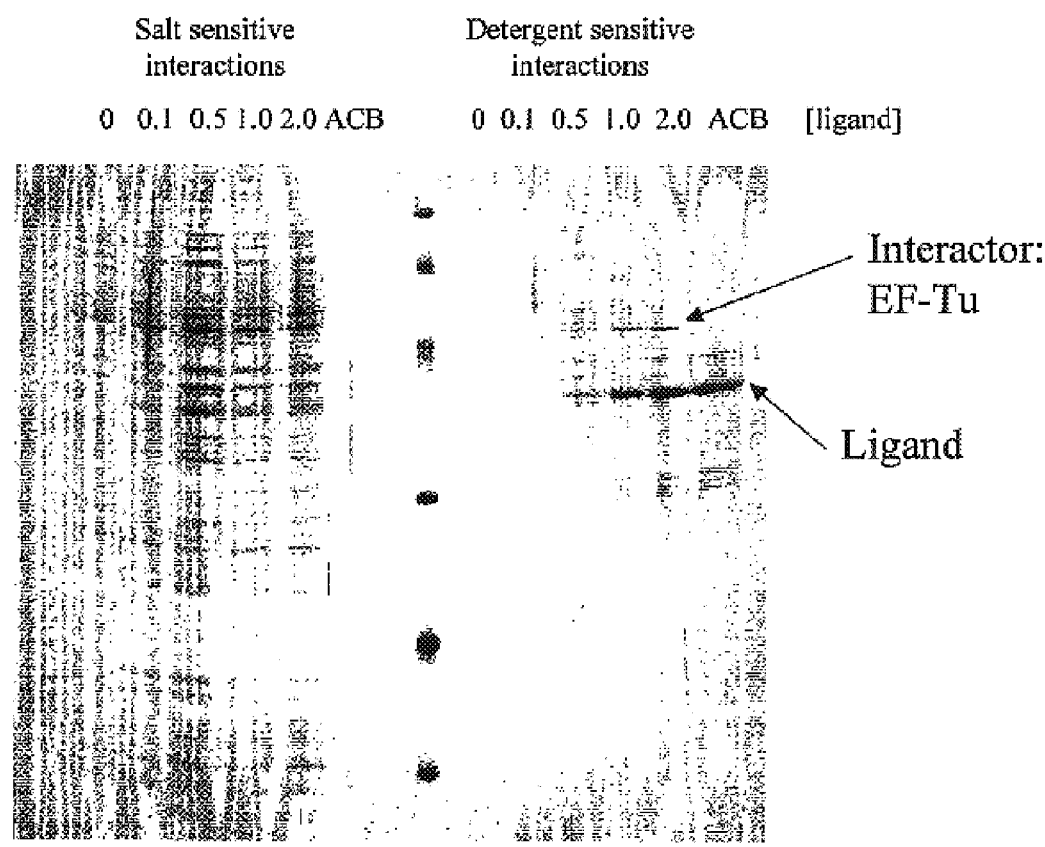
Figure 9: Interactions with SA0526

Figure 10: Interactions with SA0526
MALDI-TOF Mass Spectrum of Interactor (EF-Tu)
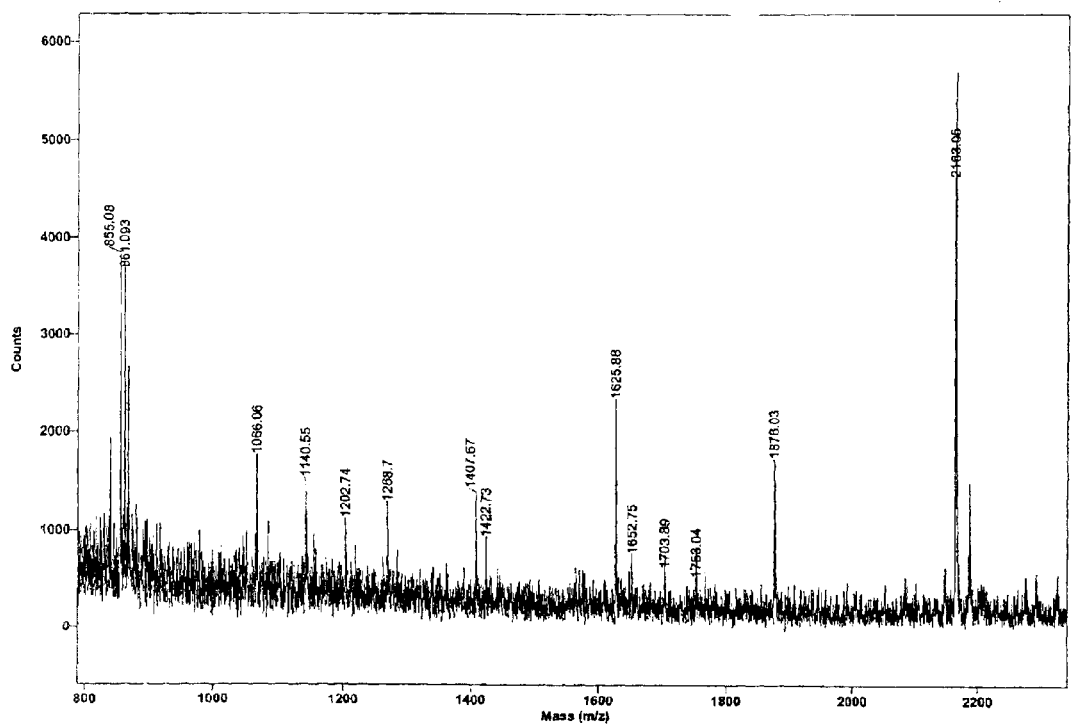

Figure 11. Interactions with SA0808
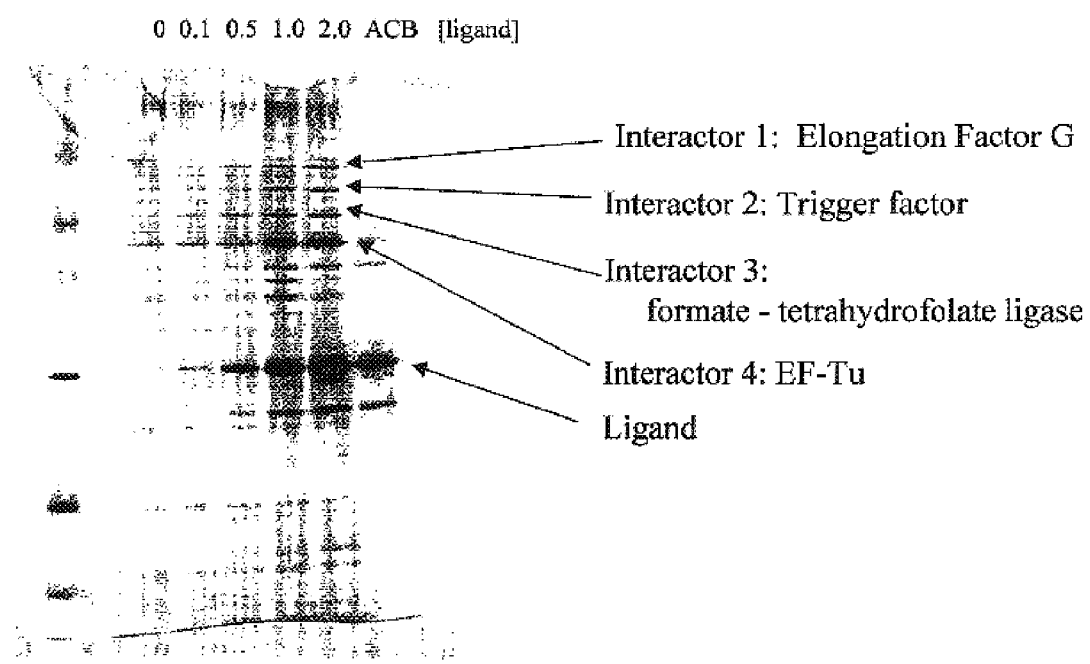

Figure 12a: Interactions with SA0808
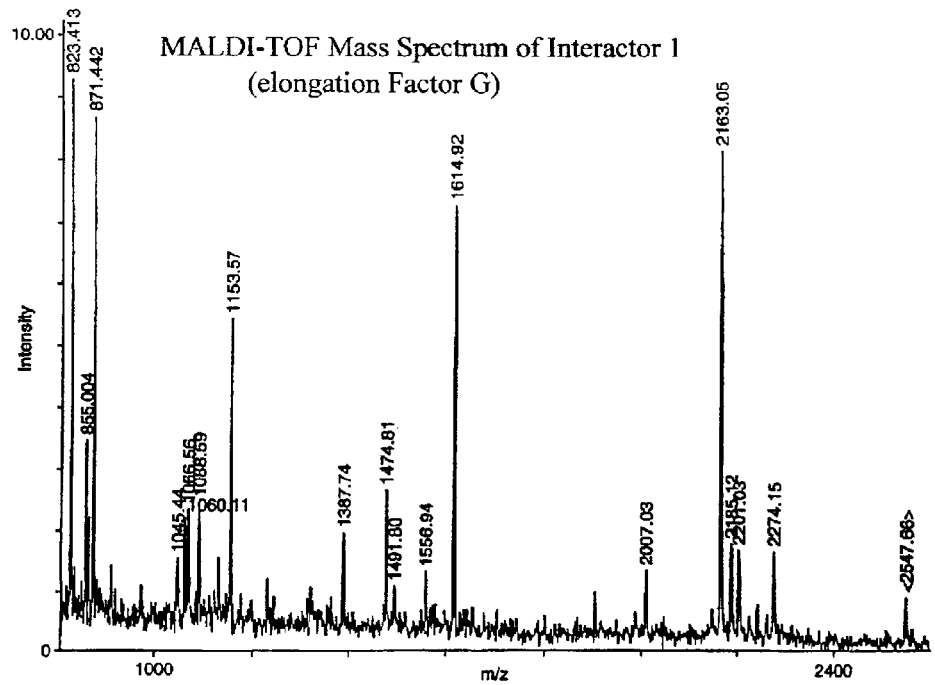
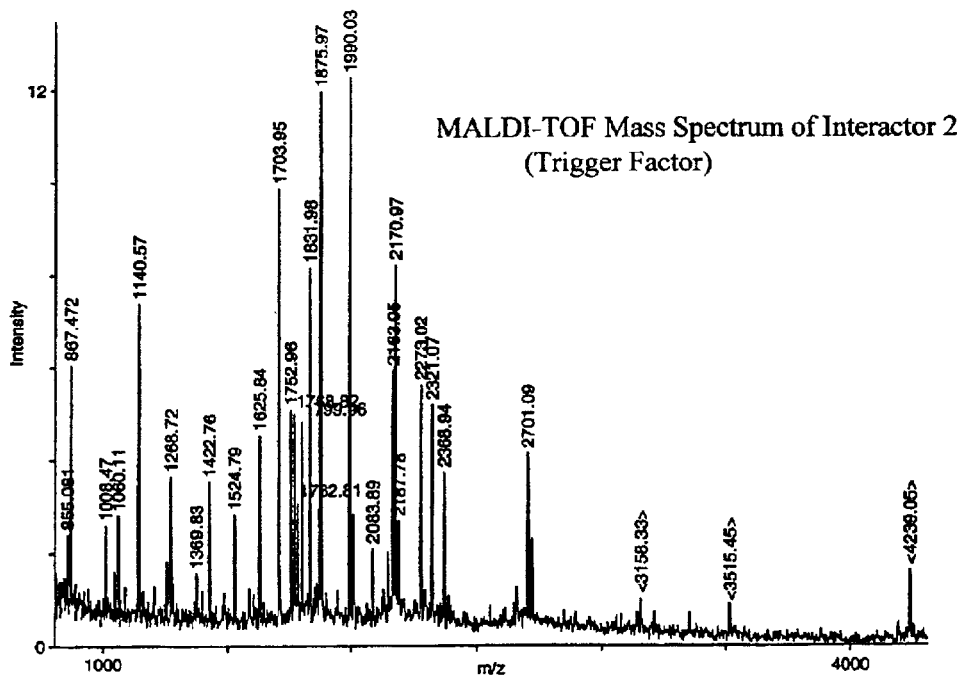

Figure 12b: Interactions with SA0808
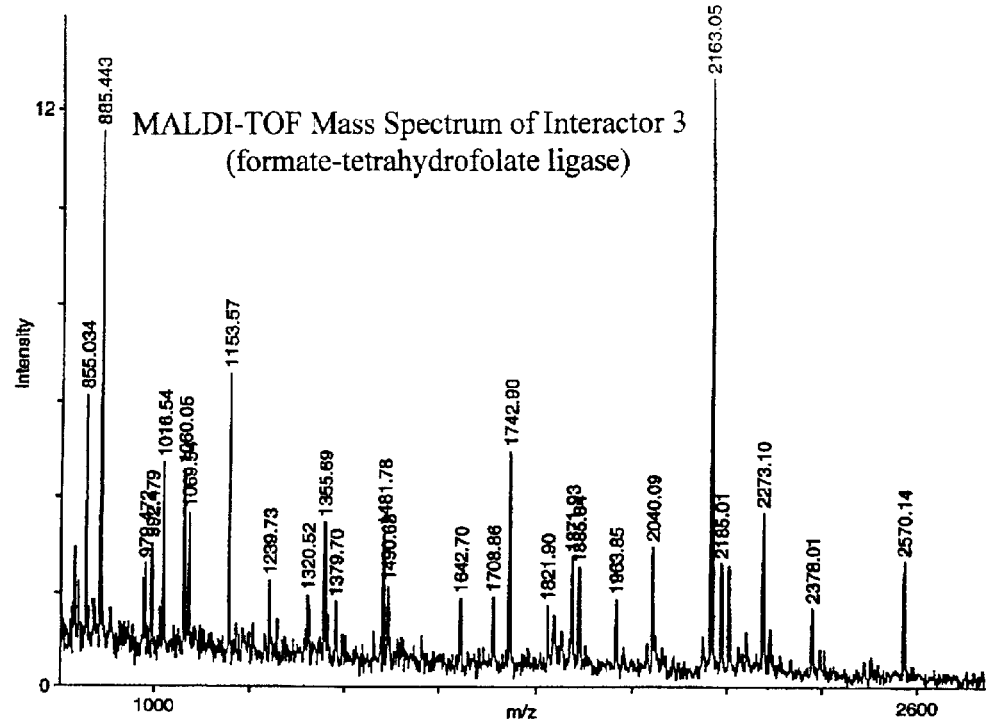
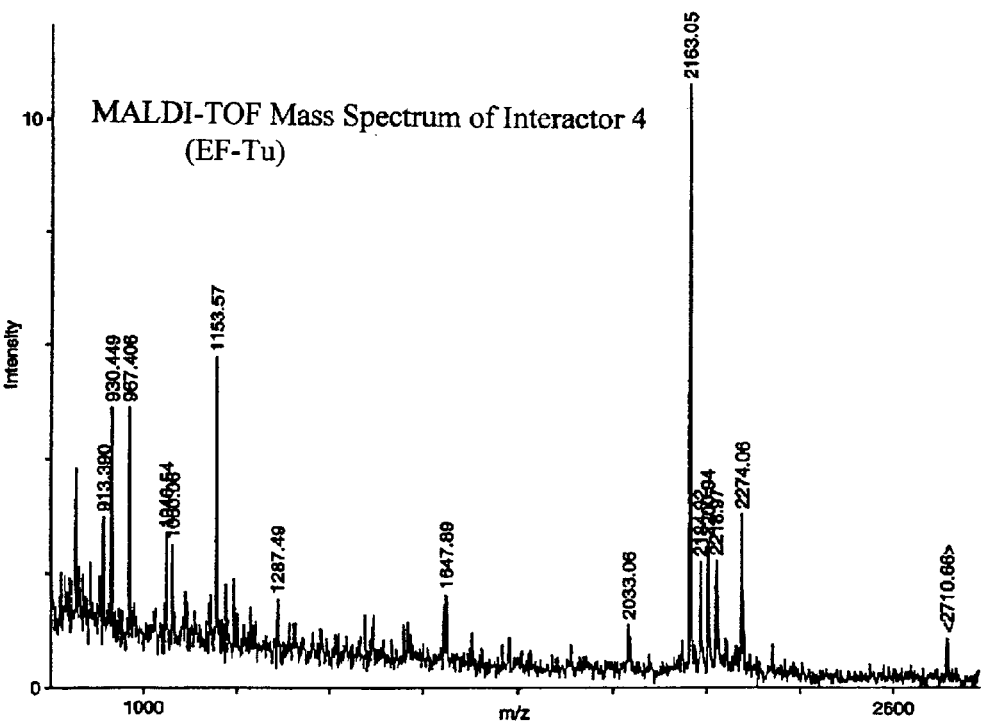

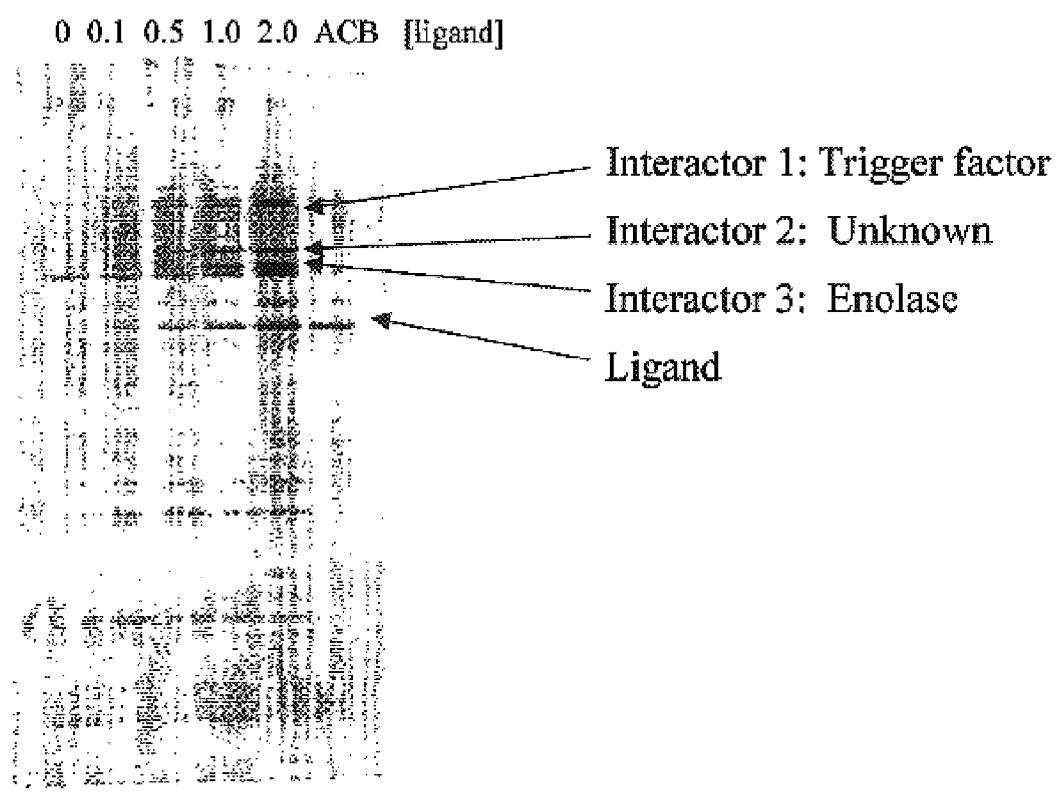
Figure 13: Interactions with SA0989

Figure 14: Interactions with SA0989
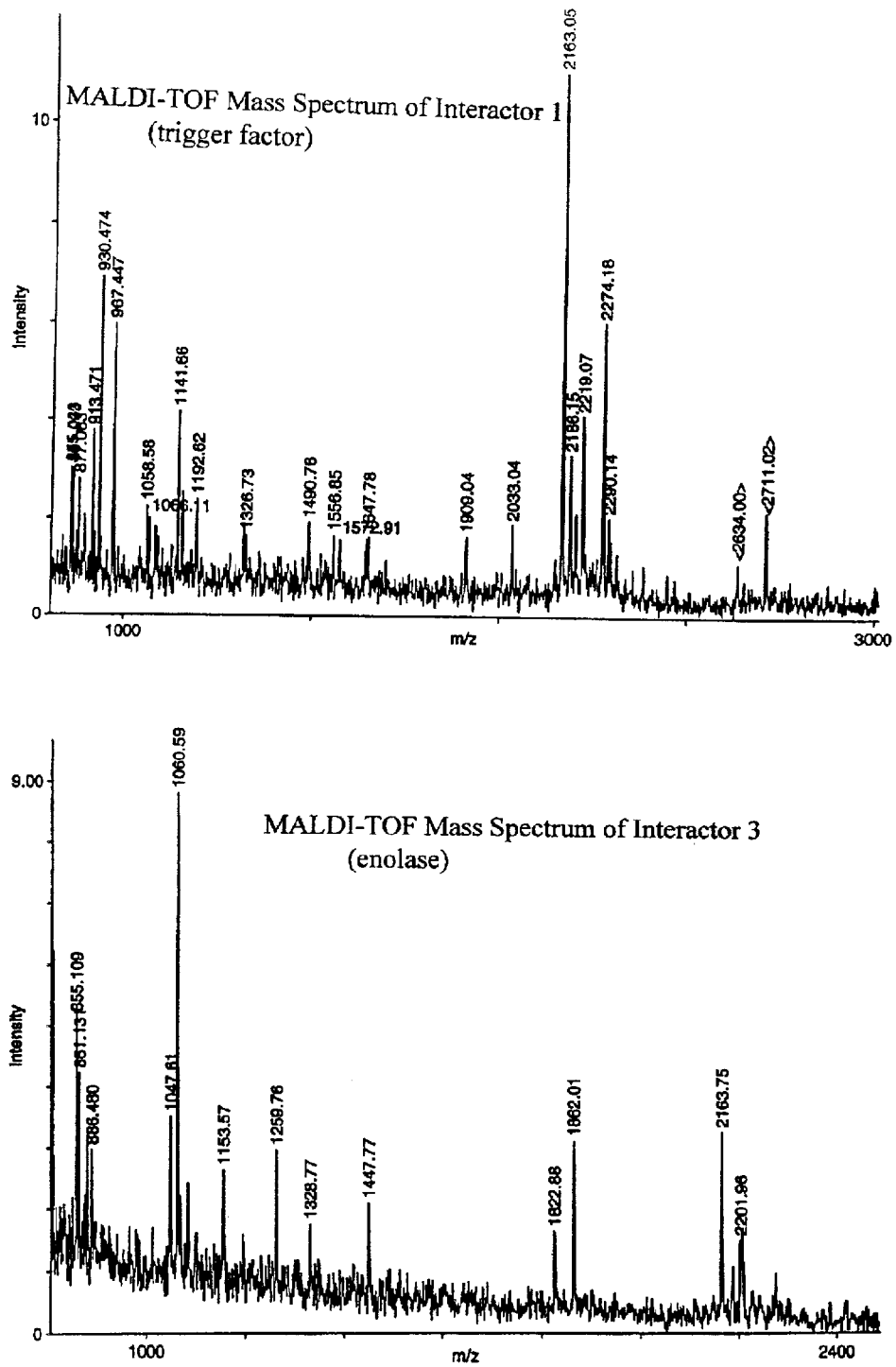

Figure 15: Interactions with SA1094
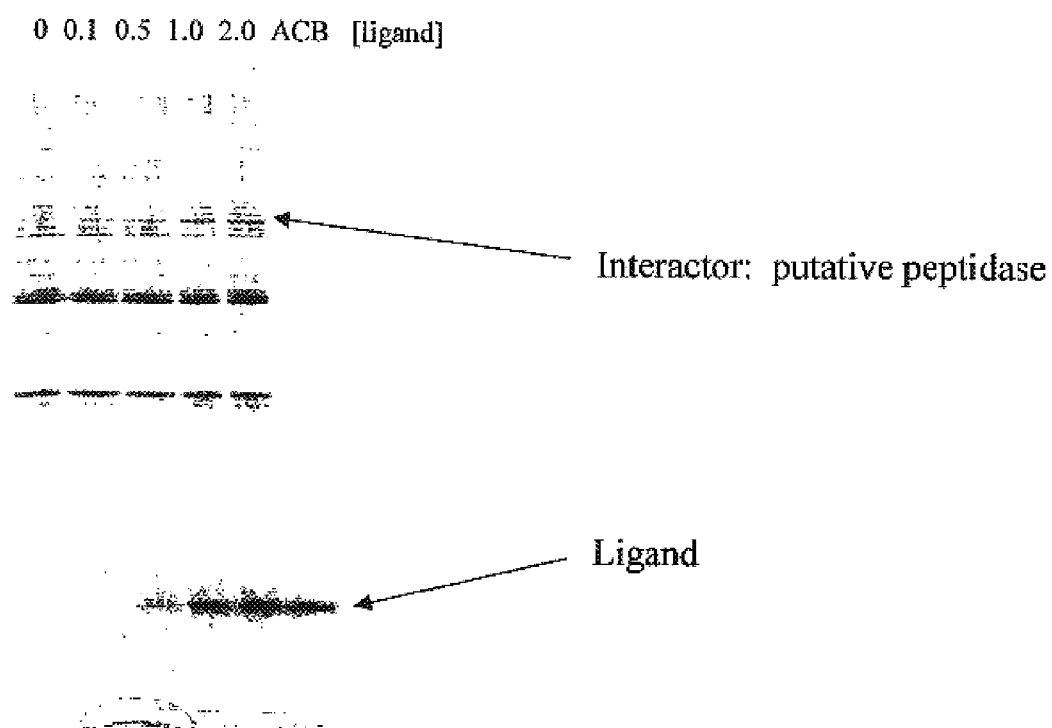

Figure 16: Interactions with SA1094
MALDI-TOF Mass Spectrum of Interactor
(putative peptidase)
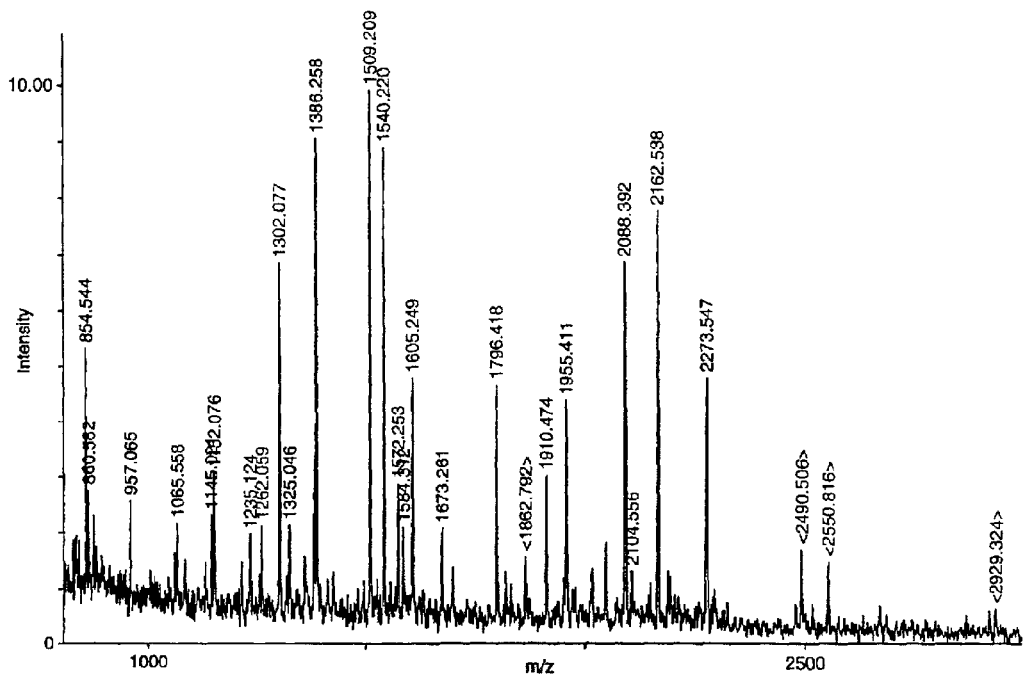

Figure 17: Interactions with SA1185
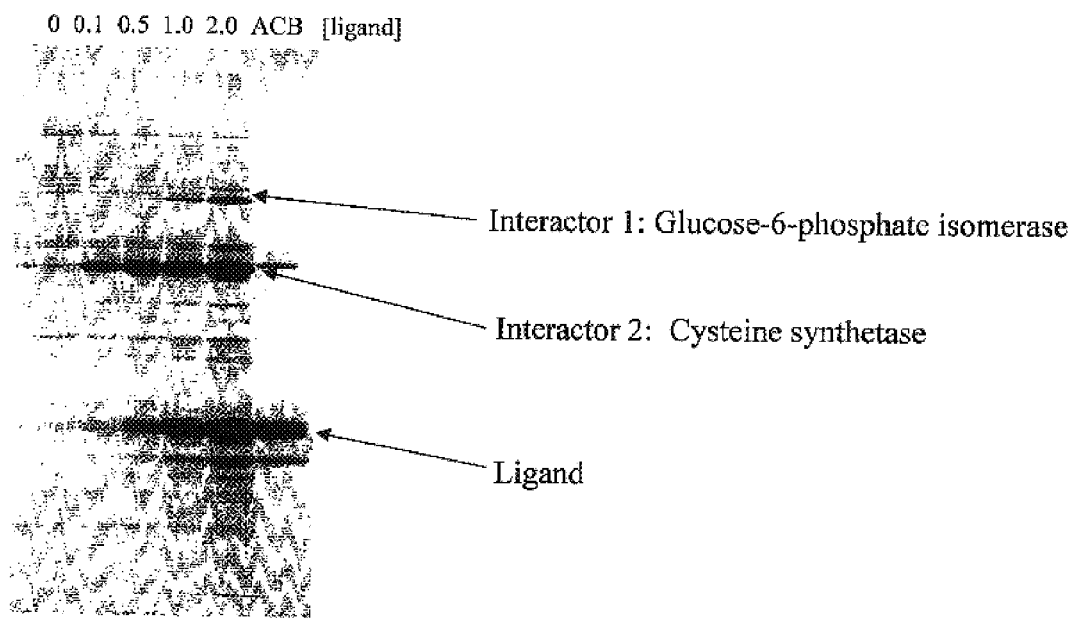

Figure 18: Interactions with SA1185
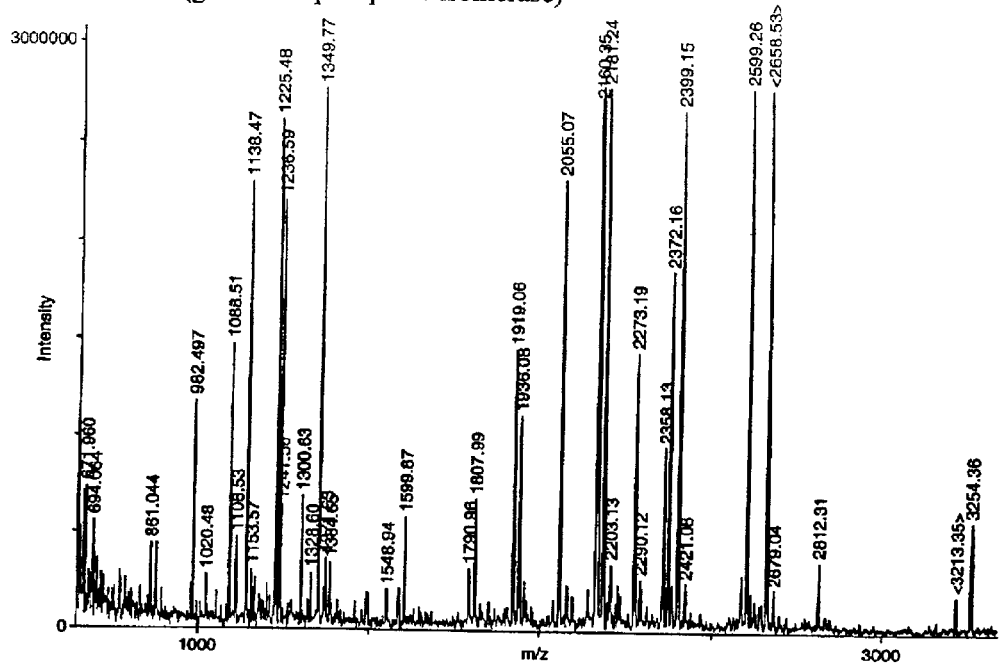
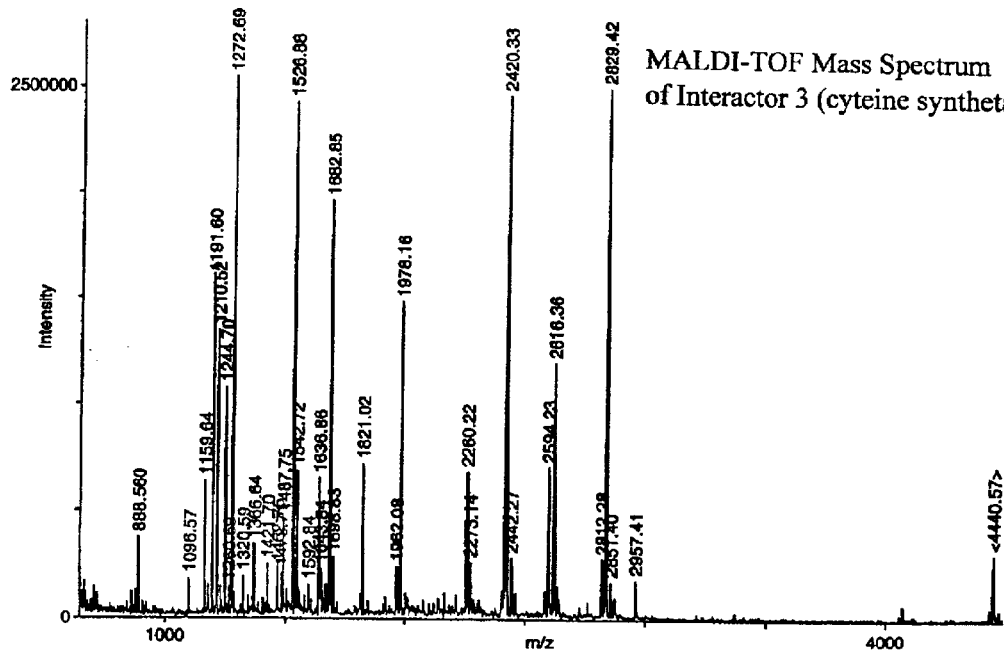

Figure 19: Interactions with SA1203
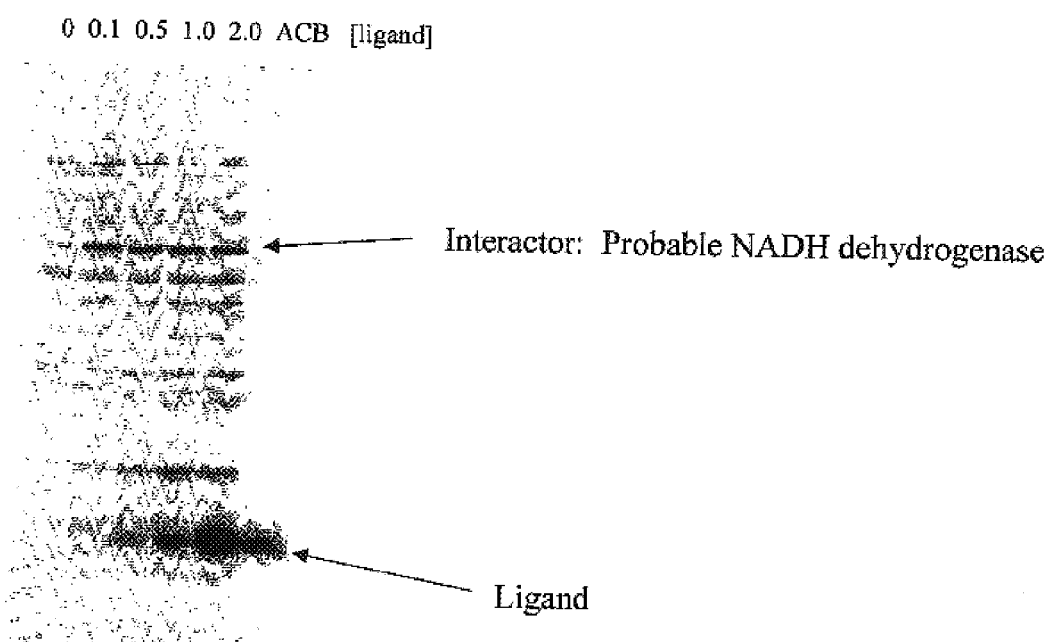

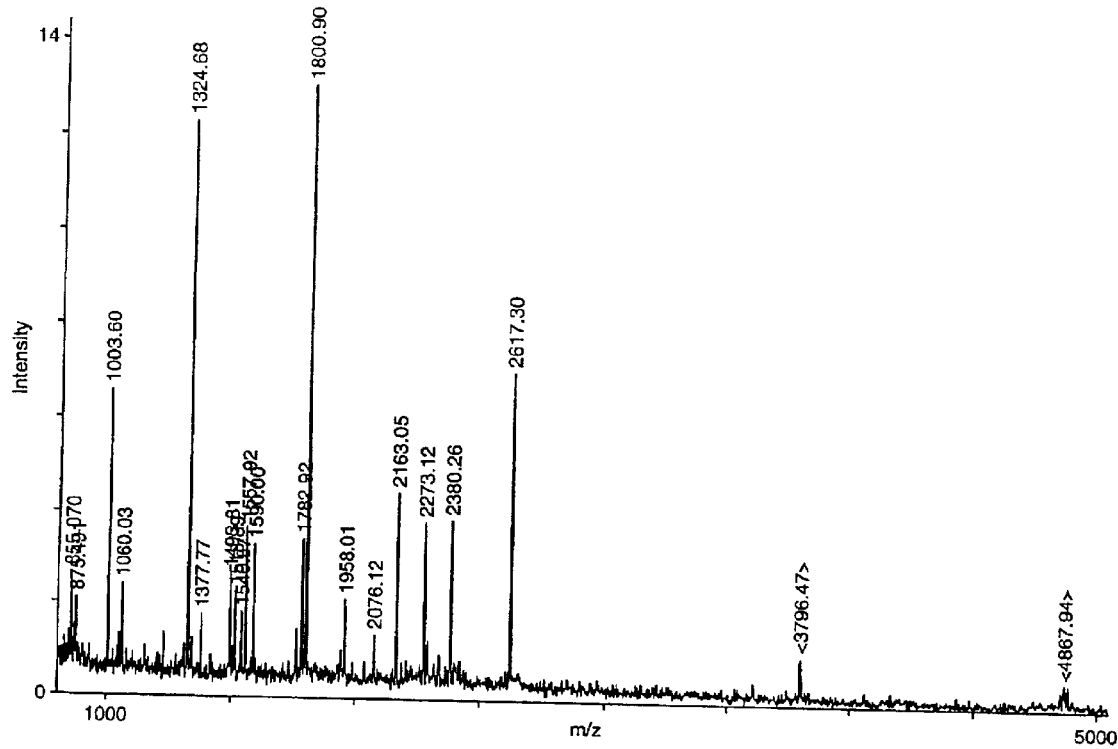
Figure 20: Interactions with SA1203
MALDI-TOF Mass Spectrum of Interactor
(probable NADH dehydrogenase)

METHODS FOR SYSTEMATIC IDENTIFICATION OF PROTEIN— PROTEIN INTERACTIONS

FIELD OF THE INVENTION

The present invention relates to a method for identifying protein—protein interactions. The interacting proteins are isolated by affinity chromatography and identified by mass spectrometry. The affinity chromatography method allows for the purification of interacting proteins which are identified using mass spectrometric techniques. The invention provides a method for the high throughput analysis of protein—protein interactions that lends itself to automation.

BACKGROUND OF THE INVENTION

The genome sequencing projects are providing vast amounts of information. With the whole genome of many organisms, including humans, complete or nearing completion, the next challenge involves the characterization of the gene products. Surprisingly, little is known about the functions of most proteins that the genes encode, or how these proteins interact to control cellular functions.

Protein interactions are intrinsic to virtually every cellular process. Most proteins in cells function in multi-subunit complexes of proteins created by specific protein—protein interactions. Many of the protein—protein interactions involved in cellular processes are too weak to allow co-purification of the interacting species by conventional methods from cellular extracts. The relatively weak binding is generally expected as proteins that must reversibly interact with each other in the concentrated intracellular environment will rapidly dissociate in a comparatively protein mixture. As the characterization of protein—protein interactions requires the in vitro reassembly of multi-subunit protein complexes, it is important to have methods for identifying and purifying all of the interacting proteins starting with one member of a protein complex.

The method of the invention uses a form of protein-affinity chromatography for the detection of protein—protein interactions. This method has been used in a non-systematic manner and has distinct advantages over other methods for the detection of protein—protein interactions, such as the two-hybrid method and co-immunoprecipitation. The two-hybrid system consists of two components, a target protein (the "bait"), fused to a DNA binding domain which binds to a specific region of DNA upstream of a reporter gene, and a protein (the "prey") fused to an activation domain which, when brought in close proximity of the reporter gene, can initiate transcription. Usually the "bait" protein is known and the "prey" protein is derived from genomic or cDNA libraries in order to isolate the interacting partner to the bait. The advantage of the two-hybrid system is that when an interactor is found the gene sequence can be determined directly. This advantage is becoming increasingly less important as the full genomic sequence of many organisms becomes available, making the identification of gene sequence from protein sequence routine. The two-hybrid system yields a very high percentage of false positives, is very labor intensive and does not easily lend itself to automation, making it a poor choice for high throughput analysis.

Protein-protein interactions have commonly been detected by antibody co-immunoprecipitation. Co-immunoprecipitation depends on the strength of a secondary protein—protein interaction, rather than on direct binding to the antibody. The technique is normally limited to relatively strong interactions with $K_d \geq 10^{-9}$ M. Additionally, it is not as sensitive as protein-affinity chromatography, because the concentration of the antigen is low.

Protein-affinity chromatography offers distinct advantages as a technique for detecting protein—protein interactions. Protein affinity chromatography allows sensitive detection of protein—protein interactions. This method can detect interactions ranging in strength from $K_d$ $10^{-5}$ to $10^{-10}$ M. This limit is within the range of the weakest interactions likely to be physiologically relevant, which is estimated to be about $10^{-3}$M. Formosa et al., Methods in Enzymology 1991, 208, 24–45. An interacting protein with a $K_d > 10^{-5}$ M may not remain bound to the column when the column is washed with buffer in order to lower the nonspecific binding of proteins from the extract to the column material.

Protein-affinity chromatography tests all proteins in an extract equally for binding to the ligand protein. Thus, extract proteins that are detected have successfully competed for the interaction with the ligand protein against the rest of the population of proteins in the extract. Additionally, interactions that are dependent on a multi-subunit complex, including the ligand protein and multiple extract proteins and/or cofactors, can be detected. Both the domains of a protein and critical residues within the protein responsible for a specific interaction can be examined for affinity to extract proteins by the use of mutant derivatives of the ligand protein.

The method of the invention allows for the isolation of specific protein interactors. The interacting proteins are identified by protease digestion followed by mass spectrometry. During the past decade, new techniques in mass spectrometry have made it possible to accurately measure with high sensitivity the molecular weight of peptides and intact proteins. These techniques have made it much easier to obtain accurate peptide masses of a protein for use in databases searches. Mass spectrometry provides a method of protein identification that is both very sensitive (10 fmol-1 pmol) and very rapid when used in conjunction with sequence databases. Advances in protein and DNA sequencing technology are resulting in an exponential increase in the number of protein sequences available in databases. As the size of DNA and protein sequence databases grows, protein identification by correlative peptide mass matching has become an increasingly powerful method to identify and characterize proteins.

Historically, the explosion in gene sequence information has far outpaced the characterization of gene products. The processes of isolation and identification of protein interactors have represented a bottleneck in the characterization of protein—protein interactions. Current methods for the isolation and identification of protein interactors are performed on a protein-by-protein basis with relatively low throughput. The method of the invention provides a process for the high throughput analysis of protein—protein interactions. The use of micro-columns and mass spectroscopy provide the basis for using high throughput methods. The use of multiple ligand concentrations provides the binding curves and assures the reliability of the interactions that are identified.

SUMMARY OF THE INVENTION

The method of the invention provides a process for the identification of interacting proteins that is suitable for high throughput analysis and amenable to automation.

The identification of protein interactions is performed using affinity chromatography followed by mass spectrometric analysis. Cellular extract or extracellular fluid is loaded onto multiple experimental micro-columns, those with bound ligand protein, and a control micro-column with no bound ligand protein. Each of the experimental micro-columns contains a different concentration of ligand bound to the matrix support. A fixed volume of cellular extract is chromatographed through each micro-column. Only affinity chromatography buffer (ACB) is chromatographed on a second control micro-column which contains the highest concentration of ligand bound (coupled) to the matrix support. The components of the eluate are separated, for example, on the basis of apparent molecular weight using SDS-PAGE, and visualized, for example, by protein staining. The interacting protein is observed to vary in amount in direct relation to the concentration of coupled protein ligand. The bands of interest are excised from the gel and analyzed using mass spectrometric techniques.

BRIEF DESCRIPTION OF THE DRAWINGS

FIG. 1 is a SDS-polyacrylamide gel run with the salt and SDS eluates from the affinity column using the *S. aureus* protein SA0005 as the ligand. The interacting protein is easily discerned from the background non-specific binding proteins as the band intensity increases with the increasing ligand concentration, but does not occur in the no-ligand and ACB controls.

FIG. 2 is the mass spectrum of the tryptic peptides of the interacting protein excised from the gel of FIG. 1. The technique used to obtain the spectrum is MALDI-TOF mass spectrometry. The peptide masses were used to identify the interacting protein as a truncated form of EF-Tu.

FIG. 3 is a SDS-polyacrylamide gel run with the salt and SDS eluates from the affinity column using the *S. aureus* protein SA0146 as the ligand. The interacting protein is easily discerned from the background non-specific binding proteins as the band intensity increases with the increasing ligand concentration, but does not occur in the no-ligand and ABC controls.

FIG. 4 is the mass spectrum of the tryptic peptides of the interacting protein excised from the gel of FIG. 3. The technique used to obtain the spectrum is MALDI-TOF mass spectrometry.

The peptide masses were used to identify the interacting protein as a concerved hypothetical protein of unknown function.

FIG. 5 is a SDS-polyacrylamide gel run with the salt and SDS eluates from the affinity column using the *S. aureus* protein SA0203 as the ligand. The interacting protein is easily discerned from the background non-specific binding proteins as the band intensity increases with the increasing ligand concentration, but does not occur in the no-ligand and ACB controls.

FIG. 6 is the mass spectrum of the tryptic peptides of the interacting protein excised from the gel of FIG. 5. The technique used to obtain the spectrum is MALDI-TOF mass spectrometry. The peptide masses were used to identify the interacting protein as a homologue of peptide chain release factor 3.

FIG. 7 is a SDS-polyacrylamide gel run with the salt and SDS eluates from the affinity column using the *S. aureus* protein SA0276 as the ligand. The interacting proteins are easily discerned from the background non-specific binding proteins as the band intensities increases with the increasing ligand concentration, but do not occur in the no-ligand and ACB controls.

FIG. 8 is the mass spectra of the tryptic peptides of the interacting proteins, interactor 1 and interactor 2, excised from the gel of FIG. 7. The technique used to obtain the spectrum is MALDI-TOF mass spectrometry. The peptide masses from the respective spectra were used to identify the interacting proteins as homologues of glutamyl-tRNA Gln amidotransferase subunits A and B.

FIG. 9 is a SDS-polyacrylamide gel run with the salt and SDS eluates from the affinity column using the *S. aureus* protein SA0526 as the ligand. The interacting protein is easily discerned from the background non-specific binding protein as the band intensity increases with the increasing ligand concentration, but does not occur in the no-ligand and ACB control.

FIG. 10 is the mass spectra of the tryptic peptides of the interacting protein excised from the gel of FIG. 9. The technique used to obtain the spectrum is MALDI-TOF mass spectrometry. The peptide masses were used to identify the interacting proteins as a homologue of EF-Tu.

FIG. 11 is a polyacrylamide gel run with SDS eluates from the affinity column using the *S. aureus* protein SA0808 as the ligand. The interacting proteins are easily discerned from the background non-specific binding protein as the band intensity increases with the increasing ligand concentration, but does not occur in the no-ligand and ACB controls.

FIGS. 12a and 12b are the mass spectra of the tryptic peptides of the interacting proteins, interactor 1, interactor 2 (FIG. 12a), interactor 3 and interactor 4 (FIG. 12b), excised from the gel of FIG. 11. The technique used to obtain the spectra is MALDI-TOF mass spectrometry. The peptide masses from the respective spectra were used to identify the interacting proteins as homologues of elongation factor G, trigger factor (prolyl isomerase), formate-tetrahydrofolate ligase, and EF-Tu.

FIG. 13 is a polyacrylarnide gel run with SDS eluates from the affinity column using the *S. aureus* protein SA0989 as the ligand. The interacting proteins are easily discerned from the background non-specific binding protein as the band intensity increases with the increasing ligand concentration, but does not occur in the no-ligand and ACB controls.

FIG. 14 is the mass spectra of the tryptic peptides of the interacting proteins, interactor 1 and interactor 3, excised from the gel of FIG. 13. The technique used to obtain the spectra is MALDI-TOF mass spectrmetry. The peptide masses from the respective spectra were used to identify two of the interacting proteins as homologues of trigger factor (prolyl isomerase) and enolase. The third is unidentified.

FIG. 15 is a polyacrylamide gel run with SDS eluates from the affinity column using the unknown *S. aureus* protein SA1094 as the ligand. The interacting protein is easily discerned from the background non-specific binding protein as the band intensity increases with the increasing ligand concentration, but does not occur in the no ligand ACB controls.

FIG. 16 is the mass spectrum of the tryptic peptides of the interacting protein excised from the gel of FIG. 15. The technique used to obtain the spectrum is MALDI-TOF mass spectrometry. The peptide masses were used to identify the interacting protein as a homologue of a putative peptidase.

FIG. 17 is a polyacrylamide gel run with SDS eluates from the affinity column using the *S. aureus* protein SA1185 as the ligand. The interacting proteins are easily discerned from the background non-specific binding protein as the band intensity increases with the increasing ligand concentration, but does not occur in the no-ligand and ACB controls.

FIG. 18 is the mass spectra of the tryptic peptides of the interacting proteins, interactor 1 and interactor 2, excised from the gel of FIG. 17. The technique used to obtain the spectra is MALDI-TOF mass spectrometry. The peptide masses from the respective spectra were used to identify the interacting proteins as homologues of glucose-6-phosphate isomerase and cysteine synthetase.

FIG. 19 is a polyacrylamide gel run with SDS eluates from the affinity column using the *S. aureus protein SA*1203 as the ligand. The interacting protein is easily discerned from the background non-specific binding protein as the band intensity increases with the increasing ligand concentration, but does not occur in the no-ligand and ACB controls.

FIG. 20 is the mass spectrum of the tryptic peptides of the interacting protein excised from the gel of FIG. 19. The technique used to obtain the spectrum is MALDI-TOF mass spectrometry. The peptide masses were used to identify the interacting protein as a homologue of NADH dehydrogenase.

DETAILED DESCRIPTION

Protein ligand

The term ligand refers to a protein to be immobilized on the column support (matrix). The possible protein ligands include naturally occurring proteins, modified proteins, synthetic proteins and subdomains or fragments of proteins. Most typically, the protein to be used as a ligand is used in a heterologous system. Ideally, the protein to be used as the ligand should be pure. Preferably, the ligand is at least 90% pure. This ensures that the interacting proteins that are detected are binding to the intended ligand rather than a contaminant. The preferred method of obtaining protein, if the gene is available, is through the use of fusion proteins. If, for technical reasons, an impure ligand must be used, it is important to use a control preparation that mimics the contaminants but does not contain ligand.

The ligand protein to be used for affinity chromatography can be encoded by the DNA of a virus or any living organism. The DNA fragment to be cloned is typically identified from the gene sequence when the genome of the organism is partly or entirely known. Isolation of the DNA fragment is performed, for example, by gel electrophoresis after digestion with a DNA restriction enzyme, by random fragmentation or by amplification from genomic DNA or a recombinant clone by using the polymerase chain reaction (PCR).

DNA encoding the protein or protein fragment is cloned into an expression vector. The wide availability of recombinant DNA technology makes it feasible to generate expression systems that can produce sufficient quantities of a selected protein for use as a ligand in the method of the invention. The steps for protein production include: generation of the protein expression systems, over-expressing the protein and purifying the protein. The generation of a clone for any particular gene of interest, and its incorporation into a suitable expression vector, is now a straightforward task that can be done in a parallel fashion for high throughput production. Edwards et al., Nature Structural Biology 2000, 7, 970–972. The selection of target proteins from completely sequenced genomes can take advantage of the availability of these cloned genes. However, even if a clone of a particular protein of interest is not readily available, it has now become a routine operation to generate a cDNA clone for almost any particular protein from a wide variety of organisms.

To obtain expression of a cloned nucleic acid, the expression vector for expression in bacteria contains a strong promoter to direct transcription, a transcription/translation terminator, and if the nucleic acid encodes a peptide or polypeptide, a ribosome binding site for translational initiation. Suitable bacterial promoters are well known in the art and described, e.g., in Sambrook et al. and Ausubel et al. Bacterial expression systems are available in, e.g., *E. coli*, Bacillus sp., and Salmonella (Palva et al., Gene 22:229–235 (1983); Mosbach et al., Nature 302:543–545 (1983). Kits for such expression systems are commercially available.

Post-translational modification of the ligand protein may be related to the protein's ability to interact with other proteins. In certain cases eukaryotic expression systems are preferred, where post-translational modifications are important, for example, glycosylation. Eukaryotic expression systems for mammalian cells, yeast, and insect cells are well known in the art and are also commercially available. In some cases, it may be preferable to employ expression vectors which can be propagated in both prokaryotic and eukaryotic cells, enabling, for example, nucleic acid purification and analysis using one organism and protein expression using another.

Transfection methods used to produce bacterial, mammalian, yeast or insect cells or cell lines that express large quantities of protein are well known in the art. These include the use of calcium phosphate transfection, polybrene, protoplast fusion, electroporation, liposomes, microinjection, viral vectors and any of the other well known methods for introducing cloned genomic DNA, cDNA, synthetic DNA or other foreign genetic material into a host cell (see, e.g., Sambrook et al., supra). After the expression vector is introduced into the cells, the transfected cells are cultured under conditions favoring expression of protein, which are then purified using standard techniques.

The protein is expressed in suitable amounts for use as the ligand. There are several expression systems that have been extensively studied. Some of these include: 1) bacterial (*E. coli*), 2) methylotrophic yeast (*Pichia pastorisis*), 3) viral (baculovirus, adenovirus, vaccinia and some RNA viruses), 4) cell culture (mammalian and insect), and 5) in vitro translation. Although the expression of any particular protein may be idiosyncratic, the availability of these and other expression systems significantly increases the ability to produce large quantities of protein.

In situations in which relatively large amounts of relatively pure protein in native form are required, it will be desirable to employ expression systems characterized by high expression levels and efficient protein processing, including cleavage of signal peptides and other post-translational modifications. The baculovirus expression system is widely used to express a variety of proteins in large quantities. In addition to fulfilling the above requirements, the size of the expressed protein is not limited, and expressed proteins are typically correctly folded and in a biologically active state. Baculovirus expression vectors and expression systems are commercially available (Clontech, Palo Alto, Calif.; Invitrogen Corp., Carlsbad, Calif.).

Once a protein has been expressed to an acceptable level, the protein is purified from the other contents of the cell system that was utilized for expression. Highly purified protein is often desirable for further analysis according to the method of the invention. The proteins can be expressed fused to tags that aid subsequent purification or measurement techniques. Typical tags bind specifically to particular affinity matrices, allowing the attached protein to be purified without regard to its physical or biochemical characteristics. Such tags can then be cleaved, leaving the protein in its native form. Examples of tags include histidine rich sequences which bind to various metal ions, glutathione-S-transferase (GST) tags which selectively bind to glutathione, maltose-binding protein, or an epitope for an available monoclonal antibody. The recombinant protein to be used as a ligand is purified from the cells of the heterologous system by a chromatographic procedure that makes use of the tag on the protein. Examples of such procedures include, but are not limited to, nickel chelate chromatography, chromatography on a glutathione column, or chromatography on a suitable antibody column. In certain cases, the fusion protein also includes a cleavable sequence of amino acids between the protein of interest and the tag sequence whereby the tag can be cleaved from the protein of interest. Typically, this is accomplished with a protease that cleaves the sequence under conditions where the protein of interest is not degraded, or with an intein sequence, which allows for internal cleavage of the protein. Alternatively, the tags provide a method for specifically anchoring proteins to a column support.

Alternatively, the ligand protein is purified by other acceptable methods known in the art, for example by immuno-chromatographic methods. Specific antibodies that recognize the ligand protein are generated in a number of organisms using ligand protein, or a portion of it. The antibodies are linked to a column support and used to purify the ligand protein from a cellular extract or other source.

The ligand protein is coupled directly (through a covalent linkage) to commercially available pre-activated resins as described in Formosa et al., Methods in Enzymology 1991, 208, 24–45; Sopta et al, J. Biol. Chem. 1985, 260, 10353–60; Archambault et al., Proc. Natl. Acad. Sci. USA 1997, 94, 14300–5. Alternatively, the ligand protein is tethered to the column support through high affinity binding interactions. If the ligand is expressed fused to a tag, such as GST, the fusion tag can be used to anchor the ligand protein to the matrix support, for example Sepharose beads containing immobilized glutathione. Column supports that take advantage of these tags are commercially available.

It is preferred that the ligand protein be coupled to the column matrix by a covalent linkage. The coupling procedures typically make use of the many primary amino groups (lysines and the amino-terminal residues) on the surface of the protein. Any coupling chemistry which makes use of primary amines is appropriate, but a reactive chemical moiety should be used which reacts at a reasonable rate at the physiological pH which is most appropriate for the ligand and the extracts to be used in the procedure (e.g., N-hydroxy-succinimide works well at pH 7.5–8.0). Commercially available column supports have reactive moieties for coupling to proteins, for example, cyanogen bromide-activated Sepharose (Pharmacia) or N-hydroxysuccinimide-activated agarose matrix, available as Affi-Gel 10 (Bio-Rad).

Failure to detect an interacting protein can result from inactivation of the ligand protein during coupling to the column support. Ideally, each ligand protein is randomly tethered to the matrix through one covalent bond. When the ligand is attached randomly, some of the immobilized protein molecules will always be oriented in such a way as to be able to interact with the proteins in the extract.

The ligand protein is contacted with the matrix under conditions that are favorable for coupling. The solid support beads are mixed and shaken gently, tumbled or rotated with solution containing the protein ligand. Alternatively, the protein ligand solution is reacted with the activated solid support which is already packed into a column. The latter method, using a pre-packed column, is preferred as it typically uses less ligand and is amenable to automation and high throughput analysis. The concentration of salt and the pH are adjusted to be appropriate for the resin and the protein ligand that are being used.

To achieve optimal sensitivity, it is important to choose a matrix that will couple a maximum concentration of protein without introducing potentially denaturing multiple cross-links to individual proteins. A matrix is chosen to minimize the non-specific interactions between proteins from the extract and the matrix. The matrix support is chosen from, for example, agarose, sepharose, glass beads, latex beads, cellulose, or dextran, To detect interactions efficiently, the concentration of the ligand protein bound to the matrix should be at least 10-fold higher than the $K_d$ of the interaction. Thus, the concentration of the ligand protein bound to the matrix should be high for the detection of weak protein—protein interactions.

The coupling is done at various ratios of the protein ligand to the resin, with the upper limit of the protein: resin ratio determined by the isoelectric point and the ionic nature of the protein. The use of a concentration series for the protein ligand allows one to obtain an estimate for the strength of the protein—protein interaction that is observed in the affinity chromatography experiment. A binding curve which has the proper shape indicates that the interaction that is observed is biologically important rather than a spurious interaction with denatured protein.

A series of columns is prepared with varying concentrations of protein ligand (mg protein ligand/ml resin volume). The number of columns employed is between 2 to 15, each with a different concentration of attached ligand. Preferably, 4 to 6 columns are prepared with varying concentrations of ligand. In addition, two control columns are generally prepared: one that contains no ligand and a second that contains the highest concentration of ligand but is not treated with extract. After elution of the columns and electrophoretic separation of the eluent components, the interacting proteins can be distinguished from the non-specific bound proteins. The concentration of the interacting proteins, as determined by the intensity of the band on the gel, will increase proportionally to the increase in protein ligand concentration but will be missing from the second control column. This allows for the identification of unknown interacting proteins.

The reaction of the protein with the solid support can be terminated, if desired, but not necessarily, by reacting the support with ethanolamine. It has been standard practice to treat the column support resin with ethanolamine and bovine serum albumin (BSA) after the ligand protein is coupled. This was done to block the remaining reactive groups on the resin. We have found that it is preferable to avoid the treatment of the resin with BSA and ethanolamine. By omitting this treatment, we have found that the non-specific binding of proteins from an extract to the resin is reduced by about five-fold.

Micro-columns

The method of the invention is ideal for small-scale analysis. A variety of column sizes, types, and geometries can be used. For high throughput analysis, it is advantageous to use small volumes, about 20–100 $\mu$l. The column can be constructed in a glass capillary with a drawn-out tip or a plastic pipette tip. In order to retain the solid support in the capillary or pipette tip, the tip is blocked with glass beads, glass wool, filter paper, or a frit. The entire affinity chromatography procedure can be automated by assembling the micro-columns into an array format (e.g. with 96 micro-column arrays or any other device containing multiple micro-columns).

Preparation of Cell Extract

The extract contains a mixture of proteins derived from a natural source. The extract may be a cellular extract or extracellular fluid. The choice of starting material for the extract is based upon the cell or tissue type or type of fluid that would be expected to contain proteins that interact with the target protein. Micro-organisms or other organisms are grown in a medium that is appropriate for that organism and can be grown in specific conditions to promote the expression of proteins that may interact with the target protein.

The starting material used to make the extract is: 1) one or more types of tissue derived from an animal, plant, or other multi-cellular organism, 2) cells grown in tissue culture that were derived from an animal or human, plant or other source, 3) micro-organisms grown in suspension or non-suspension cultures, 4) virus-infected cells, 5) purified organelles (including, but not restricted to nuclei, mitochondria, membranes, Golgi, endoplasmic reticulum, lysosomes, or peroxisomes) prepared by differential centrifugation or another procedure from animal, plant or other kinds of eukaryotic cells, 6) serum or other bodily fluids including, but not limited to, blood, urine, semen, synovial fluid, cerebrospinal fluid, amniotic fluid, lymphatic fluid or interstitial fluid.

Whole cell extracts are generally used as the source of interacting proteins. In some cases, a total cell extract may not be the optimal source of interacting proteins. For example, if the ligand is known to act in the nucleus, a nuclear extract can provide a 10-fold enrichment of proteins that are likely to interact with the ligand. In addition, proteins that are present in the extract in low concentrations can be enriched using another chromatographic method to fractionate the extract before screening various pools for an interacting protein.

The cells are lysed by standard methods, including, but not limited to enzymatic lysis, grinding with alumina or another abrasive, use of a French pressure cell, sonication, treatment with detergent, beating with glass beads in a bead beater or blender, cryogenic grinding, exposure to differential osmotic pressure, use of a mill, or use of a Dounce homogenizer. It is advantageous to carry out the procedure at a low temperature (e.g., 4° C.) in order to retard denaturation or degradation of proteins in the extract. The tissue or cells or cell extract is suspended in a solution containing Tris or Hepes or another biological buffer that is standard in the art at a concentration that is adequate to establish the pH of the extract. The pH is adjusted to be appropriate for the body fluid or tissue, cellular, or organellar source that is used for the procedure (e.g. ph7–8 for cytosolic extracts from mammals, but low pH for lysosomal extracts). The concentration of chaotropic or non-chaotropic salts in the extracting solution is adjusted so as to extract the appropriate sets of proteins for the procedure. Glycerol may be added to the lysate, as it aids in maintaining the stability of many proteins and also reduces background non-specific binding. Both the lysis buffer and column buffer should contain protease inhibitors to minimize proteolytic degradation of proteins in the extract and to protect the ligand. Appropriate co-factors that could potentially interact with the interacting proteins can be added to the extracting solution. One or more nucleases or another reagent is added to the extract, if appropriate, to prevent protein—protein interactions that are mediated by nucleic acids. Appropriate detergents or other agents are added to the solution, if desired, to extract membrane proteins from the cells or tissue. A reducing agent (e.g. dithiothreitol or 2-mercaptoethanol or glutathione or other agent) can be added to extracts derived from cells, but is more often omitted when the source of protein extract is derived from an extracellular source. Trace metals or a chelating agent can be added, if desired, to the extracting solution.

The extract is centrifuged in a centrifuge or ultracentrifuge or filtered to provide a clarified supernatant solution. This supernatant solution may be dialyzed using dialysis tubing, or another kind of device that is standard in the art, against a solution that is similar to, but may not be identical with, the solution that was used to make the extract. An example of a change in the dialysis solution is to adjust the concentrations of salts to the ones that will be used for the affinity chromatography procedure. The dialysis procedure can last from less than an hour to many hours and can be omitted for fluids derived from extracellular sources or, in some cases, for extracts derived from intracellular sources. After dialysis, the extract containing naturally occurring proteins can be used immediately, stored for a short time, stored for many hours at a low temperature or stored in a frozen state at a low temperature (e.g. −80° C.). The extract is clarified by centrifugation or filtration again immediately prior to its use in affinity chromatography.

In some cases, the crude lysate will contain small molecules that can interfere with the affinity chromatography. This can be remedied by precipitating proteins with ammonium sulfate, centrifugation of the precipitate, and re-suspending the proteins in the affinity column buffer followed by dialysis. An additional centrifugation of the sample may be needed to remove any particulate matter prior to application to the affinity columns.

The amount of cell extract applied to the column is important for two opposing reasons. If too little extract is applied to the column and the interacting protein is present at low concentration, the level of interacting protein retained by the column may be difficult to detect. Conversely, if too much extract is applied to the column, protein may precipitate on the column or competition by abundant interacting proteins for the limited amount of protein ligand may result in a difficulty in detecting minor species.

Affinity Chromatography

The columns are loaded with protein extract from an appropriate source that has been dialyzed against a buffer that is consistent with the nature of the expected interaction. Glycerol is normally included in the buffer. Any standard biological buffer can be used. The pH, salt concentrations and the presence or absence of reducing and chelating agents, trace metals, detergents, and co-factors may be adjusted according to the nature of the expected interaction. Most commonly, the pH and the ionic strength are chosen so as to be close to physiological for the source of the extract. The extract is most commonly loaded under gravity onto the columns at a flow rate of about 4–6 column volumes per hour, but this flow rate can be adjusted for particular circumstances in an automated procedure.

The volume of the extract that is loaded on the columns can be varied but is most commonly equivalent to about 5 to 10 column volumes. When large volumes of extract are loaded on the columns, there is an improvement in the signal-to-noise ratio because more protein from the extract is available to bind to the protein ligand, whereas the background binding of proteins from the extract to the solid support saturates with low amounts of extract.

A control column is included that contains the highest concentration of protein ligand, but buffer rather than extract is loaded onto this column. The elutions (eluates) from this column will contain ligand protein that failed to be attached to the column in a covalent manner, but no proteins that are derived from the extract.

The columns are washed with a buffer appropriate to the nature of the interaction being analyzed, usually, but not necessarily, the same as the loading buffer. An elution buffer with an appropriate pH, glycerol, and the presence or absence of reducing agent, chelating agent, cofactors, and detergents are all important considerations. The columns are washed with about 5 to 20 column volumes of each wash buffer to eliminate unbound proteins from the natural extract. The flow rate of the wash is usually adjusted to about 4 to 6 column volumes per hour by using gravity or an automated procedure, but other flow rates are possible in specific circumstances.

In order to elute the proteins that have been retained by the column, the interactions between the extract proteins and the column ligand are disrupted. This is performed by eluting the column with a solution of salt or detergent. Retention of activity by the eluted proteins normally requires the presence of glycerol and a good buffer of appropriate pH, as well as proper choices of ionic strength and the presence or absence of appropriate reducing agent, chelating agent, trace metals, cofactors, detergents, chaotropic agents, and other reagents. If physical identification of the bound proteins is the objective, the elution can be performed sequentially, first with buffer of high ionic strength and then with buffer containing a protein denaturant, most commonly, but not restricted to sodium dodecyl sulfate (SDS), urea, or guanidine hydrochloride. We have found that it is advantageous to simply elute the column with a protein denaturant, particularly SDS, for example as a 1% SDS solution. Using only the SDS wash, and omitting the salt wash results in SDS-gels that have higher resolution (sharper bands with less smearing). This makes it easier to visualize specifically bound proteins against the background of non-specifically bound proteins. In addition, using only the SDS wash results in half as many samples to analyze by electrophoresis. The number of samples to be analyzed is an important consideration for the development of high throughput techniques. The volume of the eluting solution can be varied but is normally about 2 to 4 column volumes. For 20 $\mu$l columns, the flow rate of the eluting procedures are most commonly about 4 to 6 column volumes per hour, under gravity, but can be varied in an automated procedure.

Separation of Eluent Components

The proteins from the extract that were bound to and are eluted from the affinity columns can be most easily resolved for identification by an electrophoresis procedure, but this procedure can be omitted and one can proceed directly to identification by mass spectrometry. Most commonly, it is easiest and most effective to use polyacrylamide gel electrophoresis (PAGE) on a slab gel, but any of the denaturing or non-denaturing electrophoresis procedures that are standard in the art can be used for this purpose, including gradient gels, capillary electrophoresis, and two-dimensional gels with isoelectric focusing in the first dimension and SDS-PAGE in the second. Preferably, the individual components in the column eluent are separated by polyacrylamide gel electrophoresis.

Protein bands or spots are visualized using a staining technique such as Coomassie blue or silver staining, or some other agent that is standard in the art that does not interfere with protein identification by mass spectrometry. Silver staining is preferred as it provides a lower detection limit, involves less time for sample preparation and does not lead to protein modifications. Alternatively, autoradiography can be used for visualizing proteins isolated from organisms cultured on media containing a radioactive label, for example $^{35}SO_4^{2-}$ or $^{35}[S]$methionine, that is incorporated into the proteins. Radioactive labeling has the advantage of allowing detection and quantitation by scintillation counting of fractions containing binding proteins before polyacrylamide gel electrophoresis. Additionally, the use of radioactively labelled extract allows a distinction to be made between extract proteins that were retained by the column and proteolytic fragments of the ligand that may be released from the column. However, radioactive labeling is relatively expensive without being more sensitive than silver staining. The radioactive extracts must be handled more carefully, and autoradiography is generally slower than silver staining.

Protein bands that are derived from the extract (i.e. it did not elute from the control column that was not loaded with protein from the extract) and bound to an experimental column that contained protein ligand covalently attached to the solid support, and did not bind to a control column that did not contain any protein ligand, are excised from the stained electrophoretic gel with a clean instrument, usually a scalpel, and further processed for mass spectrometry.

Identification of the protein by mass spectrometry is greatly facilitated if the disulfide bonds of the protein are reduced and the free thiols are alkylated after reduction and prior to digestion of the protein with protease. The reduction is performed by treatment of the gel slice with a reducing agent, for example with dithiothreitol. The protein is alkylated by treating the gel slice with a suitable alkylating agent, for example iodoacetamide.

Prior to analysis by mass spectrometry, the protein may be chemically or enzymatically digested. The protein sample in the gel slice is subjected to in-gel digestion. Shevchenko A. et al., Mass Spectrometric Sequencing of Proteins from Silver Stained Polyacrylamide Gels. Analytical Chemistry 1996, 58, 850–858. The preferred method of digestion is by treatment with the enzyme trypsin. The resulting peptides are extracted from the gel slice into a buffer.

The peptide fragments may be purified, for example by use of chromatography. A solid support that differentially binds the peptides and not the other compounds derived from the gel slice, the protease reaction or the peptide extract may be used. The peptides are eluted from the solid support into a small volume of a solution that is compatible with mass spectrometry (e.g. 50% acetonitrile/0.0% trifluoroacetic acid).

The preparation of a protein sample from a gel slice that is suitable for mass spectrometry can also be done by an automated procedure.

Mass Spectrometry

Peptide samples derived from gel slices can be analyzed by any one of a variety of techniques in mass spectrometry, including, but not limited to matrix-assisted laser desorption ionization time-of-flight mass spectrometry (MALDI-TOF), triple quadrupole MS using either electrospray MS, electrospray tandem MS, nano-electrospray MS, or nano-electrospray tandem MS, as well as ion trap or Fourier transform mass spectrometry, or mass spectrometers comprised of components from any one of the above mentioned types (e.g. quadrupole-TOF). This analysis can be performed with any mass spectrometer that has the capability of measuring the peptide masses with high mass accuracy, precision, and resolution, as well as the capability of measuring the masses of fragments generated from a specific peptide when analyzed under conditions that induce dissociation of the peptide.

Eluates from the affinity chromatography columns can also be analyzed directly without resolution by electrophoretic methods, by proteolytic digestion with a protease in solution, followed by applying the proteolytic digestion products to a reverse phase column and eluting the peptides from the column directly into a mass spectrometer using an electrospray or nano-electrospray sample introduction interface. For example, peptides may be eluted directly into an ion trap or triple quadrupole mass spectrometer.

Methods that use a MALDI-TOF instrument are, however, more rapid and preferred for high throughput procedures because it takes approximately 30 seconds to analyze a sample by MALDI-TOF in an automated procedure, whereas it takes approximately one hour to introduce samples into the other kinds of instruments via micro-capillary HPLC.

If MALDI-TOF is used to analyze the peptides from the digested interacting protein, the method yields a high accuracy peptide mass spectrum. Patterson, Electrophoresis 1995, 16, 1104–14. The peptide masses obtained from MALDI-TOF are used for correlative database searching of protein or DNA sequence databases. Yates et al., Anal. Biochem. 1993, 214, 397–408. The molecular weights of the peptides are compared with a database of peptides from predicted proteins encoded by the organism's genome. This sensitive method is able to characterize proteins that are present at very low concentration, as low as sub-picomole levels. This method is suitable for high throughput identification of proteins, particularly for organisms whose genomes are sequenced.

This method allows the rapid and accurate mapping of peptide mixtures by measuring the molecular weight of each component. The peptide mixture is generated by sequence-dependent cleavage of the polypeptide backbone by proteolytic enzymes or chemical agents. The peptide map obtained by specific cleavage or digestion, for example with trypsin, results in a unique peptide fingerprint for a given protein. Thus in the case of mass spectrometric mapping, the experimental data are a partial or complete set of molecular weights of peptides resulting from the cleavage (digestion) of the protein. The peptide masses are searched against both in-house proprietary and public databases using a correlative mass matching algorithm. Statistical analysis is performed upon each protein match to determine the validity of the match. Typical constraints include error tolerances within 0.1 Da for monoisotopic peptide masses. Cysteines are alkylated and searched as carboxyamidomethyl modifications. Identified proteins are stored automatically in a relational database with software links to SDS-PAGE images and ligand sequences. Often, even a partial peptide map is specific enough for identification of the protein. If no match is found, a more error-tolerant search can be used, for example using fewer peptides or allowing a larger margin for error. In these cases the tentative identity of the interacting protein should be confirmed by a second method.

This technique is used to assign function to an unknown protein based upon the known function of the interacting protein in the same or a homologous/orthologous organism. Protein-protein interactions are stored in a relational database to create an 'in-silico' network of protein interactions with the predicted effect each protein has upon cellular functions.

The knowledge gained from the relational database is used to select protein targets for further analysis including the immobilization of one or more interacting partners on a solid support and screening a chemical or drug library for compounds that affect the interaction. The chemicals or drugs are screened for there ability to influence the protein—protein interaction.

Tandem mass spectrometry or post source decay is used for proteins that cannot be identified by peptide-mass matching or to confirm the identity of proteins that are tentatively identified by an error-tolerant peptide mass search, described above. This method combines two consecutive stages of mass analysis to detect secondary fragment ions that are formed from a particular precursor ion. The first stage serves to isolate a particular ion of a particular peptide (polypeptide) of interest based on its m/z. The second stage is used to analyze the product ions formed by spontaneous or induced fragmentation of the selected ion precursor. Interpretation of the resulting spectrum provides limited sequence information for the peptide of interest. However, it is faster to use the masses of the observed peptide fragment ions to search an appropriate protein sequence database and identify the protein as described in Griffin et al, Rapid Commun. Mass. Spectrom. 1995, 9, 1546–51.

Peptide fragment ions are produced primarily by breakage of the amide bonds that join adjacent amino acids. The fragmentation of peptides in mass spectrometry has been well described (Falick et al., J. Am Soc. Mass Spectrom. 1993, 4, 882–893; Biemann, K., Biomed. Environ. Mass Spectrom. 1988, 16, 99–111)

The following examples are provided as illustrative of the present invention and are not limiting.

EXAMPLE 1

Protein SA0005

A protein from the bacterium *Staphylococcus aureus*, labeled SA0005, was chosen for use as the ligand. SA0005 was determined to have high homology to heat shock protein 33, a putative chaperone involved in protein folding.

Production of SA0005

A bioinformatics program (A. L. Delcher, D. Harmon, S. Kasif, 0. White, and S. L. Salzberg. Improved microbial gene identification with GLIMMER, Nucleic Acids Research, 1999, 27:, 4636–4641) is used to select the coding sequence of interest from the genome of *S. aureus*. The coding DNA is amplified from purified genomic DNA by using PCR with primers that are identified with a computer program. The PCR primers are selected so as to introduce restriction enzyme cleavage sites at the ends of the DNA (e.g. Nde1 and BamH1). The PCR product is purified by gel electrophoresis and directionally cloned into the polylinker of the expression vector pET15b (Novagen, Wis.) after the polylinker is cut with the same two restriction enzymes. After the ligation reaction, the DNA is transformed into *E. coli* bacteria that will allow the production of the recombinant protein in high yield. The expression vector uses a promoter for the RNA polymerase of bacteriophage T7, and the strain of *E. coli* is able to produce T7 RNA polymerase when isopropyl-β-D-thiogalactoside (IPTG) is added to the growth medium. The sequence of the cloning site is such as to add polyhistidine, followed by a cleavage site for the enzyme thrombin, to the amino-terminal of the recombinant heterologous protein. Bacteria containing the recombinant plasmid are selected for by antibiotic resistance, indicating they have acquired the plasmid, and identified either by using PCR or another method to analyze their DNA or by using SDS-PAGE or mass spectrometry to identify clones that produce the desired protein in large amounts.

A clone that produces the desired recombinant heterologous protein in large amounts is grown in Luria broth or another mediun. IPTG is added when the culture has reached an appropriate cell density and then the culture is incubated overnight at 15° C., harvested by centrifugation at 5000 rpm for 15 minutes, and broken by sonication. The extract is clarified by centrifugation at 15000 rpm for 30 minutes.

Nucleic acid is removed from the clarified extract by passing the extract through a DE52 column in a buffer containing 500 mM NaCl. The recombinant protein is then bound to a nickel column and eluted with buffer containing imidazole. After the imidazole is removed from the preparation by dialysis, the tag is removed from the protein by digestion with thrombin and the mixture is passed through another nickel column. The recombinant heterologous protein without the polyhistidine tag flows through the second nickel column, now highly purified and ready for use in affinity chromatography.

Staphylococcus Aureus Extract Preparation:

A *Staphylococcus aureus* extract is prepared from cell pellets using nuclease and lysostaphin digestion followed by sonication. A *Staphylococcus aureus* cell pellet (12 g) is suspended in 12 ml of 20 mM Hepes pH 7.5, 150 mM NaCl, 10% glycerol, 10 mM $MgSO_4$, 10 mM $CaCl_2$, 1 mM DTT, 1 mM PMSF, 1 mM benzamidine, 1000 units of lysostaphin, 0.5 mg RNAse A, 750 units micrococcal nuclease, and 375 units DNAse 1. The cell suspension is incubated at 37° C. for 30 minutes, cooled to 4° C., and is made up to a final concentration of 1 mM EDTA and 500 mM NaCl. The lysate is sonicated on ice using three bursts of 20 seconds each. The lysate is centrifuged at 20 000 rpm for 1 hr in a Ti70 fixed angle Beckman rotor. The supernatant is removed and dialyzed overnight in a 10 000 Mr dialysis membrane against ACB (20 mM Hepes pH 7.5, 10% glycerol, 1 mM DTT, and 1 mM EDTA) containing 100 mM NaCl, 1 mM benzamidine, and 1 mM PMSF. The dialyzed protein extract is removed from the dialysis tubing and frozen in one ml aliquots at −70° C.

Preparation of Affinity Column

A series of solutions of the ligand (SA0005) is prepared so as to give final amounts of 0, 0.1, 0.5, 1.0, and 2.0 mg of ligand per ml of resin volume. Assuming that the stock solution of ligand has a concentration of 3.5 mg/ml the following samples are prepared in labelled silanized microcentifuge tubes:

| ligand conc. on resin | 0 | 0.1 | 0.5 | 1 | 2 |
| --- | --- | --- | --- | --- | --- |
| volume of resin (µl) | 100 | 100 | 100 | 100 | 100 |
| Protein (µg) | 0 | 10 | 50 | 100 | 200 |
| protein (µl) | 0.0 | 2.9 | 14.5 | 28.9 | 57.8 |
| ACB buffer (µl) | 300 | 297.1 | 285.5 | 271.1 | 242.2 |

A slurry of Affigel 10 is prepared and 1 ml of slurry is removed (enough for six 100-µl aliquots of resin). Using a glass frit Buchner funnel, the resin is washed sequentially with three 10 ml portions each of ice-cold isopropanol, distilled $H_2O$, and ACB containing 1 M NaCl. The resin is completely drained of buffer, but not dried. Into six clean silanized microcentrifuge tubes is added 100 mg of the Affigel 10. The buffer containing the ligand concentration series, as shown in the table, is added to the tubes containing Affigel 10 and mixed gently. The tubes containing the coupling reactions are places on a rotator at 4° C. overnight. After coupling, the Affigel 10 resin is centrifuged at 2000 rpm for 1 minute at 4° C., or alternatively, the beads are allowed to settle under gravity. The beads are isolated by removing the supernatant solution which is saved for later analysis to evaluate the coupling efficiency.

To the Affigel 10 is added 300 µl of ACB containing 100 mM NaCl and 80 mM ethanolamine. The Affigel 10 is resuspended and rotated for 2 hours at 4° C. The remaining reactive groups react with the ethanolamine. The Affigel 10 resin is centrifuged at 2000 rpm for 1 minute at 4° C., or the beads are allowed to settle under gravity. The supernatant is removed and discarded. As an option, add 300 µl of ACB containing 100 mM NaCl and 1 mg/ml of bovine serum albumin, resuspend the beads, and rotate for 2 hours. The Affigel 10 resin is centrifuged at 2000 rpm for 1 minute at 4° C., or allowed to settle under gravity, and the supernatant is removed and discarded. The resin is resuspended in 300 µl of ACB containing 1 M NaCl. This step is repeated 3 times to wash away the free bovine serum albumin from the resin. The supernatant is removed and the resin is resuspended with 100 µl of ACB containing 100 mM NaCl.

The micro-columns are prepared by using forceps to bend the ends of P200 pipette tips. To the pipette tips is added 10 µl of glass beads and 80 µl of a 50% slurry of the Affigel 10 resin containing the covalently attached ligand protein. The columns are allowed to drain on ice in a 1.5 ml microcentrifuge tube and are washed with 10 column volumes (400 µl) of ACB containing 100 mM NaCl.

Affinity Chromatography

Ten column volumes of the *S. aureus* extract is added to each micro-column and the flow-throughs of the columns are removed when approximately 50–100 µl accumulates. Each column is washed in the same manner with 5 column volumes of ACB containing 100 mM NaCl. This washing is repeated once. Each column is washed with 5 column volumes of ACB containing 100 mM NaCl and 0.1% Triton X-100. The columns are eluted sequentially with 4 column volumes of ACB containing 1M NaCl and 4 column volumes of 1% sodium dodecyl sulfate into clean microcentrifuge tubes. To each eluted fraction is added one-tenth volume of 10-fold concentrated loading buffer for SDS-PAGE.

Resolution of the Eluted Proteins and Detection of Bound Proteins

The components of the eluted samples are resolved on SDS-polyacrylamide gels containing 13.8% polyacrylamide using the Laemmli buffer system.

After the electrophoresis procedure is complete, the gel is stained in a clean glass tray. Using 500 ml of each rinse solution, the gel is treated sequentially with 1) 50% methanol, 10% acetic acid overnight or for at least two hours to fix the gel. Repeat once for 20 minutes, 2) 20% ethanol for 10 minutes, 3) distilled water for 10 minutes, 4) sodium thiosulfate (0.2 g/liter) for 1 minute to reduce the gel, 5) water, twice for 20 seconds each wash, 6) silver nitrate (2.0 g/liter) for 30 minutes, and 7) water for 20 seconds. The gel is washed once with developing solution (50 to 75 ml) for 30 seconds, and is developed to the desired intensity, until the band is visible (a light to dark brown). The developing solution contains sodium carbonate (30 g/liter), formaldehyde (1.4 ml of 37% solution/liter), and sodium thiosulfate (10 mg/liter). Once the desired stain intensity has been reached, the developing solution is removed quickly. The reaction is stopped by adding a 1% acetic acid solution and incubating for a minimum of 20 minutes. The gel is rinsed with 1% acetic acid.

The gel is shown in FIG. 1. One interacting protein is apparent from the 1% SDS eluates.

The bands containing the interacting protein are excised with a clean scalpel. The gel volume is kept to a minimum by cutting as close to the band as possible. The gel slice is placed into a clean 0.5 ml microcentrifuge tube. To the gel slices is added 10 to 20 µl of 1% acetic acid. The sample can be stored frozen at −70° C. for an extended period of time.

Sample Preparation for Mass Spectrometry

The gel slices are cut into 1 mm cubes and 10 to 20 µl of 1% acetic acid is added. The gel particles are washed with 100–150%1 of HPLC grade water (5 minutes with occasional mixing), briefly centrifuged and the liquid is removed. Acetonitrile (~200 μl, approximately 3 to 4 times the volume of the gel particles) is added followed by incubation at room temperature for 10 to 15 minutes with occasional mixing. A second acetonitrile wash may be required to completely shrink the gel particles. The sample is briefly centrifuged and all the liquid is removed.

The protein in the gel particles is reduced by covering the gel slices with 100 mM ammonium bicarbonate containing 10 mM dithiothreitol and incubating at 50° C. for 30 minutes. Briefly centrifuge and remove all the liquid. Acetonitrile is added to shrink the gel particles and the excess liquid is removed. The protein in the gel particles is alkylated by covering the gel particles with 100 mM ammonium bicarbonate containing 55 mM iodoacetamide and incubating for 20 minutes at room temperature in the dark. The sample is briefly centrifuged and all the liquid is removed. The gel particles are washed with 150 to 200 μl of 100 mM ammonium bicarbonate for 15 minutes with occasional mixing. The sample is briefly centrifuged and all the liquid is removed. Acetonitrile is added to shrink the gel particles and the excess liquid is removed. The sample is briefly centrifuged and all the liquid is removed. The gel particles are dried using a centrifugal vacuum concentrator for 1 minute.

To digest the interacting protein, the gel particles are rehydrated in digestion buffer containing trypsin (50 mM ammonium bicarbonate, 5 mM $CaCl_2$, and 12.5 ng/ul trypsin) on ice for 30 to 45 minutes (after 20 minutes incubation more trypsin solution is added). The excess trypsin solution is removed and 10 to 15 μl digestion buffer without trypsin is added to ensure the gel particles remain hydrated during digestion. The samples are incubated at 37° C. overnight.

The samples are briefly centrifuged and all the liquid is transferred to a clean microcentrifuge tube (0.5 ml)(step 1). To the gel particles is added 100 μl of 100 mM ammonium bicarbonate and the peptides are extracted by shaking at 37° C. in an orbital shaker for 30 minutes followed by centrifugation. The liquid (step 2) is pooled with the liquid from step 1. A second portion of 100 μl of 100 mM ammonium bicarbonate is added to the gel particles and the peptides are extracted a second time by shaking at 37° C. in an orbital shaker for 30 minutes followed by centrifugation. The liquid is pooled with the liquid from steps 1 and 2.

Purification of the Tryptic Peptides

Bulk C18 reverse phase resin is washed several times with methanol and with 65% acetonitrile prior to use and a 5:1 slurry is prepared with 65% acetonitrile/1% acetic acid. Five μl of the C18 slurry are added to the extracted peptides and shaken for 30 minutes at 37° C. The supernatant is removed and 150 μl of 2% acetonitrile/1% acetic acid are added and shaken for 5 to 15 minutes at 37° C. All of the supernatant is removed and 10 to 15 μl of 65% acetonitrile/1% acetic acid are added. The sample is vortexed briefly and incubated for 5 minutes with occasional mixing. The sample is centrifuged and the supernatant is removed to a fresh tube for analysis by mass spectrometry.

Mass Spectrometric Analysis

Analytical samples containing tryptic peptides are subjected to Matrix Assisted Laser Desorption/Ionization Time Of Flight (MALDI-TOF) mass spectrometry. Samples are initially mixed with an equal volume of organic solvent containing a compound (matrix) that ionizes peptides upon excitation by a laser pulse. The matrix could be one of α-cyano-4-hydroxy-trans-cinnamic acid, sinnipinic acid, or 2,5-dihydroxybenzoic acid. The mixture of the sample and matrix is allowed to dry on a sample stage and introduced into the mass spectrometer. Specifically, 0.5 μl matrix solution containing 20 mg/ml α-cyano-4-hydroxy-trans-cinnamic acid in 50% acetonitrile/1 % acetic acid is mixed with 0.5 μl sample and applied to a well of a multi-sample MALDI-TOF plate. Analysis of the peptides in the mass spectrometer is carried out using delayed extraction and an ion reflector to ensure high resolution of peptides. The instrument is initially calibrated using the autohydrolysis peaks generated by trypsin, but the method is not dependent upon trypsin and any protease having a defined cleavage specificity may be used.

Tryptic peptide masses are searched against both in-house proprietary and public databases using a correlative mass matching algorithm. Twenty peptide masses were used in the search. Statistical analysis is performed upon each protein match to determine the validity of the match. Typical constraints include error tolerances within 0.1 Da for monoisotopic peptide masses. Cysteines are alkylated and are searched as carboxyamidomethyl modifications. Identified proteins are stored automatically in a relational database with software links to SDS-PAGE images and ligand sequences. The tryptic peptide mass spectrum is shown in FIG. 2.

The closest protein match from the correlative search and the probability of a correct match for the five closest protein matches are shown in Table 1.

TABLE 1

Results of correlative database searching of 20 peptide masses.

| Rank | Probability | Name |
|------|-------------|------|
| 1 | 1.0e+00 | EF-Tu |
| 2 | 1.0e−17 | |
| 3 | 7.7e−18 | |
| 4 | 1.4e−18 | |
| 5 | 2.0e−19 | |

One interacting protein was discovered and identified as a truncated form of EF-Tu, whose intact form is a key factor involved in protein biosynthesis. This form of EF-Tu is novel. It is most likely made by intracellular proteolysis from intact EF-Tu. It could be involved in protein synthesis in *S. aureus* or could have some other function. The chaperone, if it is one, could be involved in the folding of the EF-Tu fragment or in its assembly with some other protein. Examples 2–5 are performed using the procedures of Example 1.

EXAMPLE 2

Protein SA0146

A protein from the bacterium *Staphylococcus aureus*, labeled SA0146, was chosen for use as the ligand. SA0146 was found to be a homolog of the *B. subtilis* cell division initiation protein, DIV IVA, which is involved in septum formation.

TABLE 2

Results of correlative database searching of 14 peptide masses.

| Rank | Probability | Name |
|------|-------------|------|
| 1 | 1.0e+00 | conserved protein of unknown function |
| 2 | 1.7e−11 | |

TABLE 2-continued

Results of correlative database searching of 14 peptide masses.

| Rank | Probability | Name |
|---|---|---|
| 3 | 4.0e−12 | |
| 4 | 8.5e−13 | |
| 5 | 8.2e−13 | |

The interacting protein was found to be a conserved protein of unknown function. The data suggests that the interacting conserved protein is also involved in cell division. It could be a good drug target because cell division is an essential process.

EXAMPLE 3

Protein SA0203

An unknown protein from the bacterium *Staphylococcus aureus*, labeled SA0203, was chosen for use as the ligand. The function of SA0203 is unknown.

TABLE 3

Results of correlative database searching of 15 peptide masses.

| Rank | Probability | Name |
|---|---|---|
| 1 | 1.0e+00 | peptide chain release factor 3 |
| 2 | 2.4e−07 | |
| 3 | 2.5e−08 | |
| 4 | 1.1e−08 | |
| 5 | 8.1e−09 | |

The interacting protein was found to be a homologue of peptide chain release factor 3. Its interaction with peptide chain release factor 3 suggests that it is involved in the termination stage of protein synthesis. It could potentially be a good drug target because many antibiotics inhibit protein synthesis.

EXAMPLE 4

Protein SA0276

A protein from the bacterium *Staphylococcus aureus*, labeled SA0276, was chosen for use as the ligand. Because of its high homology to other bacterial homologues, SA0276 was labeled a putative phenylalanine tRNA synthetase subunit, although only part of its sequence is a good match to enzymes of that type in other species.

TABLE 4

Identification of Interactor 1, results of correlative database searching of 29 peptide masses.

| Rank | Probability | Name |
|---|---|---|
| 1 | 1.0e+00 | glutamyl-tRNA Gln amidotransferase subunit B |
| 2 | 7.7e−22 | |
| 3 | 6.3e−22 | |
| 4 | 5.1e−23 | |
| 5 | 6.4e−24 | |

TABLE 5

Identification of Interactor 2, results of correlative database searching of 23 peptide masses.

| Rank | Probability | Name |
|---|---|---|
| 1 | 1.0e+00 | glutamyl-tRNA Gln amidotransferase subunit A |
| 2 | 1.9e−13 | |
| 3 | 1.3e−14 | |
| 4 | 3.4e−15 | |
| 5 | 1.7e−15 | |

Two interacting proteins were discovered and identified as homologues of glutamyl-tRNA Gln amidotransferase subunits A and B.

In *S. aureus* and perhaps other organisms, SA0276 may have an additional function in which it interacts with a portion of glutamyl tRNA and acts as a cofactor for glutamyl-tRNA glutamine amidotransferase. If so, that might have a vital function outside of charging phenylalanine tRNA, and chemicals that inhibit that activity could be good antibiotics.

EXAMPLE 5

Protein SA0526

A protein from the bacterium *Staphylococcus aureus*, labeled SA0526, was chosen for use as the ligand. SA0526 was determined to be a homologue of EF-Ts, a protein synthesis elongation factor that is conserved in all bacteria.

TABLE 6

Results of correlative database searching of 14 peptide masses.

| Rank | Probability | Name |
|---|---|---|
| 1 | 1.0e+00 | EF-Tu |
| 2 | 4.6e−12 | |
| 3 | 3.7e−12 | |
| 4 | 1.6e−13 | |
| 5 | 1.4e−13 | |

The interacting protein was found to be a homologue of EF-Tu. The interaction of EF-Tu with EF-Ts, which is confirmed in this experiment, has been known for more than 30 years.

EXAMPLE 6

Protein SA0808

A protein from the bacterium *Staphylococcus aureus*, labeled SA0808, was chosen for use as the ligand. SA0808 was determined to be homologous to menaquinone biosynthesis methyltransferase, an enzyme involved in the last step in the synthesis of menaquinone (vitamin K).

SA0808 was prepared in a manner analogous to example 1.

*S. aureus* Extract Preparation:

A *S. aureus* cell pellet (~12 g) is suspended in 20 ml of lysis buffer (20 mM Hepes pH 7.5, 500 mM NaCl, 10% glycerol, 10 mM $MgSO_4$, 10 mM $CaCl_2$, 1 mM DTT, 1 mM EDTA, 1 mM PMSF, 1 mM benzamidine). The nucleases Rnase A (40 ug/ml final) and micrococcal nuclease (75 units/mL) are added. The cells are lysed with 10 pulses of 30 sec. between 90 sec. pauses using the Bead-Beater apparatus (Biospec Products Inc.). The outer chamber of the apparatus is filled with ice and the inner chamber with a 50/50 mixture of cells and zirconia beads (0.1 mm diameter). The lysate is separated from the zirconia beads using a standard chromatography column and peristalic pump. The lysate is centrifuged at 20000 rpm (48000× g) in Oak Ridge tubes (50 mL capacity) in a Beckman JA25.50 rotor. The extract is dialyzed against 1 L of 0.1 M ACB (20 mM Hepes pH 7.5, 100 mM NaCl, 10% glycerol, 10 mM $MgSO_4$, 10 mM $CaCl_2$, 1 mM DTT, 1 mM EDTA, 1 mM PMSF, 1 mM benzamidine) overnight at 4° C. in a dialysis membrane (Spectrum Labs, 10 kDa size exclusion). The extract is removed from the dialysis membrane and stored in 1 mL aliquots at −80° C.

Preparation of Affinity Column

A series of solutions of the ligand (SA0808) is prepared so as to give final amounts of 0, 0.1, 0.5, 1.0, and 2.0 mg of ligand per ml of resin volume. Assuming that the stock solution of ligand has a concentration of 3.5 mg/ml the following samples are prepared in labelled silanized microcentifuge tubes:

| ligand conc. on resin | 0 | 0.1 | 0.5 | 1 | 2 |
|---|---|---|---|---|---|
| volume of resin (μl) | 100 | 100 | 100 | 100 | 100 |
| Protein (μg) | 0 | 10 | 50 | 100 | 200 |
| protein (μl) | 0.0 | 2.9 | 14.5 | 28.9 | 57.8 |
| ACB buffer (μl) | 300 | 297.1 | 285.5 | 271.1 | 242.2 |

A slurry of Affigel 10 is prepared and 1 ml of slurry is removed (enough for six 100-μl aliquots of resin). Using a glass frit Buchner funnel, the resin is washed sequentially with three 10 ml portions each of ice-cold isopropanol, distilled $H_2O$, and ACB containing 1 M NaCl. The resin is completely drained of buffer, but not dried. Into six clean silanized microcentrifuge tubes is added 100 mg of the Affigel 10. The buffer containing the ligand concentration series, as shown in the table, is added to the tubes containing Affigel 10 and gently mixed to suspend the resin. The tubes containing the coupling reactions are places on a rotator at 4° C. overnight. After coupling, the Affigel 10 resin is centrifuged at 2000 rpm for 1 minute at 4° C. The beads are isolated by removing the supernatant solution. The supernatant of the 2 mg/ml reaction is saved for later analysis to evaluate the coupling efficiency.

To remove any free ligand, the resin is resuspended with 1 M ACB, centrifuged at 2000 rpm, and the supernatant is removed. This is repeated twice more. The resin is resuspended with 100 μL of 0.1 M ACB.

The micro-columns are prepared by using forceps to bend the ends of P200 pipette tips. To the pipette tips is added 10 μl of glass beads and 80 μl of a 50% slurry of the Affigel 10 resin containing the covalently attached ligand protein. The micro-columns are allowed to drain on ice in a 1.5 ml microcentrifuge tube. The micro-columns are adjusted to 40 μl of resin (50 μl mark on tip) and are washed with 5 column volumes of ACB containing 100 mM NaCl.

Affinity Chromatography

The extract is centrifuged in a microcentrifuge tube at 15000 rpm for 15 minutes at 4° C. The supernatant is removed to a fresh microcentrifuge tube and diluted to 5 mg protein/ml ACB containing 100 mM NaCl.

Five column volumes of the *S. aureus* extract is added to each micro-column and the flow-throughs of the columns are removed when approximately 50–100 μl accumulates. Each column is washed in the same manner with 5 column volumes of ACB containing 100 mM NaCl. This washing is repeated once. Each column is washed with 5 column volumes of ACB containing 100 mM NaCl and 0.1% Triton X-100. The columns are eluted sequentially with 4 column volumes of 1% sodium dodecyl sulfate into clean microcentrifuge tubes. To each eluted fraction is added one-tenth volume of 10-fold concentrated gel loading buffer.

Resolution of the Eluted Proteins and Detection of Bound Proteins

The components of the eluted samples are resolved on polyacrylamide gels (no SDS is present in the gel, with 0.1% present in the gel running buffer) containing 13.8% polyacrylamide.

The gels are stained by silver staining using a mass spectrometry compatible protocol, as in Example 1. The gel is shown in FIG. 11.

The bands of interest are excised with a clean scalpel. The gel volume is kept to a minimum by cutting as close to the band as possible. The gel slice is placed into a clean 0.5 ml microcentrifuge tube. To the gel slices is added 10 to 20°l of 1% acetic acid. The sample can be stored frozen at −70° C. for an extended period of time.

Sample Preparation for Mass Spectrometry

The interacting proteins in the excised bands are digested with trypsin, and the resulting peptides are purified according to the procedures of Example 1.

Mass Spectrometric Analysis

The tryptic peptides are analyzed using MALDI-TOF mass spectrometry according to the procedures of Example 1. The tryptic peptide masses are searched against both in-house proprietary and public databases using a correlative mass matching algorithm. Statistical analysis is performed upon each protein match to determine the validity of the match. Typical constraints include error tolerances within 0.1 Da for monoisotopic peptide masses. Cysteines are alkylated and are searched as carboxyamidomethyl modifications. Identified proteins are stored automatically in a relational database with software links to SDS-PAGE images and ligand sequences. The tryptic peptide mass spectra for the four interating proteins are shown in FIGS. 12a and 12b. The closest protein match from each correlative search and the probability of a correct match for the five closest protein matches are shown in Tables 7–10.

TABLE 7

Identification of Interactor 1, results of correlative database searching of 27 peptide masses.

| Rank | Probability | Name |
|---|---|---|
| 1 | 1.0e+00 | elongation factor G |
| 2 | 1.2e−28 | |
| 3 | 2.4e−30 | |
| 4 | 1.7e−30 | |
| 5 | 1.6e−30 | |

TABLE 8

Identification of Interactor 2, results of correlative database searching of 21 peptide masses.

| Rank | Probability | Name |
|---|---|---|
| 1 | 1.0e+00 | trigger factor (prolyl isomerase) |
| 2 | 2.9e−10 | |
| 3 | 1.4e−10 | |
| 4 | 7.1e−11 | |
| 5 | 5.0e−11 | |

TABLE 9

Identification of Interactor 3, results of correlative database searching of 19 peptide masses.

| Rank | Probability | Name |
|---|---|---|
| 1 | 1.0e+00 | formate-tetrahydrofolate ligase |
| 2 | 1.9e−07 | |
| 3 | 7.3e−08 | |
| 4 | 2.9e−08 | |
| 5 | 1.8e−08 | |

TABLE 10

Identification of Interactor 4, results of correlative database searching of 29 peptide masses.

| Rank | Probability | Name |
|---|---|---|
| 1 | 1.0e+00 | EF-Tu |
| 2 | 1.3e−27 | |
| 3 | 7.0e−28 | |
| 4 | 1.0e−28 | |
| 5 | 3.2e−29 | |

Four interacting proteins are discovered and identified by MALDI-TOF mass spectrometry and correlative database searching as homologues of elongation factor G, trigger factor (prolyl isomerase), formate-tetrahydrofolate ligase, and EF-Tu.

SA0808 is homologous to an enzyme involved in the last step in the synthesis of menaquinone (vitamin K). Its involvement in single carbon transfer as a methyltransferase could explain its interaction with formate-tetrahydrofolate ligase, an enzyme involved in one-carbon metabolism, but the exact connection is obscure. SA0808 also interacts with trigger factor, which is a prolyl isomerase. The prolyl isomerase could be involved in the proper folding of SA0808 or could have some other role in its activity. There is genetic evidence for the possible involvement of the homologue of SA0808 of *B. subtilis* in spore germination, which involves the restart of a variety of metabolic processes, including protein synthesis. That could suggest that SA0808 has a previously unsuspected function in which it interacts with and perhaps modifies the protein synthesis factors EF-Tu and EF-G in order to control their activities. Interfering with this interaction could be a way to control the germination of bacteria.

Examples 7–10 are performed using the procedures of Example 6.

EXAMPLE 7

Protein SA0989

A protein from the bacterium *Staphylococcus aureus*, labeled SA0989, is chosen for use as the ligand. SA0989 was determined to be homologous to 3-methyl-2-oxobutanoate dehydrogenase.

TABLE 12

Identification of Interactor 1; Results of correlative database searching of 24 peptide masses.

| Rank | Probability | Name |
|---|---|---|
| 1 | 1.0e+00 | trigger factor (prolyl isomerase) |
| 2 | 2.4e−20 | |

TABLE 12-continued

Identification of Interactor 1; Results of correlative database searching of 24 peptide masses.

| Rank | Probability | Name |
|---|---|---|
| 3 | 1.9e−21 | |
| 4 | 7.7e−22 | |
| 5 | 7.7e−22 | |

TABLE 13

Identification of Interactor 3; Results of correlative database searching of 13 peptide masses.

| Rank | Probability | Name |
|---|---|---|
| 1 | 1.0e+00 | enolase |
| 2 | 1.4e−07 | |
| 3 | 7.5e−08 | |
| 4 | 6.0e−08 | |
| 5 | 7.5e−09 | |

Three interacting proteins are discovered Two are identified by MALDI-TOF mass spectrometry as homologoes of trigger factor (prolyl isomerase) and enolase. The third is unidentified.

SA0989 is probably a branched chain α-ketoacid dehydrogenase involved in the second step in the synthesis of branched chain amino acids. Trigger factor is a prolyl isomerase which could be involved in the folding of SA0989. SA0989 also interacts with another protein that has not yet been positively identified and with enolase. Although the interaction with enolase could have some significance that we do not appreciate, enolase has been found to bind to at least 20 of the proteins of *S. aureus*. Although it is possible that enolase has a chaperone-like function for many other proteins, it is also possible that enolase is a protein that interacts with many proteins in a fashion that is not biologically important.

EXAMPLE 8

Protein SA1094

A protein from the bacterium *Staphylococcus aureus*, labeled SA1094, is chosen for use as the ligand. SA1094 is a protein of heretofore unknown function.

TABLE 14

Results of correlative database searching of 29 peptide masses.

| Rank | Probability | Name |
|---|---|---|
| 1 | 1.0e+00 | putative petidase |
| 2 | 1.7e−19 | |
| 3 | 1.7e−21 | |
| 4 | 3.9e−22 | |
| 5 | 2.1e−22 | |

One interacting protein is discovered. The interactor is found to be a homologue of a putative peptidase.

The interaction of SA1094 with a putative peptidase (based on homologues in other organisms) suggests that SA1094 is likely to be involved in peptide metabolism.

EXAMPLE 9

Protein SA1185

A protein from the bacterium *Staphylococcus aureus*, labeled SA1185, is chosen for use as the ligand. SA1185 is a protein of heretofore unknown function.

TABLE 15

Identification of Interactor 1; Results of correlative database searching of 39 peptide masses.

| Rank | Probability | Name |
|---|---|---|
| 1 | 1.0e+00 | glucose-6-phosphate isomerase |
| 2 | 3.1e−36 | |
| 3 | 2.6e−36 | |
| 4 | 1.1e−36 | |
| 5 | 5.6e−37 | |

TABLE 16

Identification of Interactor 2; Results of correlative database searching of 35 peptide masses.

| Rank | Probability | Name |
|---|---|---|
| 1 | 1.0e+00 | cysteine synthetase |
| 2 | 7.9e−40 | |
| 3 | 1.3e−41 | |
| 4 | 5.1e−43 | |
| 5 | 2.1e−43 | |

Two interacting proteins are discovered. The identities of the interactors are determined by MALDI-TOF mass spectrometry as homologues of glucose-6-phosphate isomerase and cysteine synthetase.

SA1185 interacts with two enzymes of widely differing functions, glucose-6-phosphate isomerase involved in glucose metabolism and cysteine synthetase involved in the last step in cysteine biosynthesis. SA1185 could be involved in controlling the activities or localizations of both enzymes.

EXAMPLE 10

Protein SA1203

A protein from the bacterium *Staphylococcus aureus*, labeled SA1203, is chosen for use as the ligand. SA1203 is a protein of heretofore unknown function.

TABLE 12

Results of correlative database searching of 21 peptide masses.

| Rank | Probability | Name |
|---|---|---|
| 1 | 1.0e+00 | NADH dehydrogenase. |
| 2 | 1.9e−14 | |
| 3 | 3.6e−16 | |
| 4 | 4.2e−17 | |
| 5 | 2.9e−17 | |

One interacting protein is discovered. The interacting protein is a homologue of NADH dehydrogenase.

SA1203's specific interaction with the respiratory enzyme NADH dehydrogenase suggests it could be involved in respiration and controlling the activity or membrane versus cytosolic location of that enzyme.

What is claimed is:

1. A method for the identification of an interacting protein, said method comprising:
   a) subjecting an extract to protein-affinity chromatography on two or more columns in parallel, said columns having a protein ligand in varying concentrations immobilized to a matrix, and eluting bound components of said extract from the immobilized protein ligand;
   b) separating said components to isolate an interacting protein;
   c) selecting an interacting protein from said components, wherein the amount of said interacting protein eluting from said columns varies proportionately with the concentration of immobilized ligand; and
   d) analyzing the interacting protein by mass spectrometry to identify the interacting protein.

2. The method of claim 1, wherein said columns are micro-columns.

3. The method of claim 1, wherein said separation is a gel-separation.

4. The method of claim 3, wherein said gel-separation is a polyacrylamide gel electrophoresis.

5. The method of claim 4, wherein said polyacrylamide gel contains SDS.

6. The method of claim 1, wherein said protein ligand is covalently bound to the matrix.

7. The method of claim 1, wherein said mass spectrometry is matrix-assisted laser desorption ionization time-of-flight (MALDI-TOF) mass spectrometry.

8. The method of claim 1, wherein the bound components of the extract are eluted with a protein denaturant.

9. The method of claim 1, wherein the protein ligand is immobilized to the matrix after the matrix has been packed into the column.

10. The method of claim 2, wherein multiple micro-columns are arranged into an array format.

11. The method of claim 1, wherein the columns are not blocked after immobilizing the ligand to the matrix.

12. The method of claim 1, wherein the protein-affinity chromatography is an automated process.

13. The method of claim 1, wherein the protein ligand is at least 90% pure.

14. The method of claim 1, wherein the protein ligand is a fusion protein.

15. The method of claim 14, wherein the fusion protein comprises an affinity tag which may be used to couple the protein ligand onto the matrix.

16. The method of claim 1, wherein the concentration of the protein ligand bound to the matrix in at least one of the columns is at least 10-fold higher than the $K_d$ of the interaction between the protein ligand and the interacting protein.

17. The method of claim 1, wherein the concentration of the protein ligand bound to the matrix is from 0 to about 2 milligrams of ligand per milliliter of matrix for all of the columns.

18. The method of claim 1, wherein the extract is derived from a tissue, cultured cell line, purified cellular organelle, or bodily fluid.

19. The method of claim 1, wherein the extract is a whole cell extract or a fractionated extract.

* * * * *